US012646620B2

(12) United States Patent
Patek

(10) Patent No.: US 12,646,620 B2
(45) Date of Patent: Jun. 2, 2026

(54) JOINT STATE ESTIMATION PREDICTION THAT EVALUATES DIFFERENCES IN PREDICTED VS. CORRESPONDING RECEIVED DATA

(71) Applicant: Dexcom, Inc., San Diego, CA (US)

(72) Inventor: Stephen D. Patek, Charlottesville, VA (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 17/096,763

(22) Filed: Nov. 12, 2020

(65) Prior Publication Data

US 2021/0151141 A1 May 20, 2021

Related U.S. Application Data

(60) Provisional application No. 62/935,920, filed on Nov. 15, 2019.

(51) Int. Cl.
*G16H 20/17* (2018.01)
*A61B 5/00* (2006.01)
(Continued)

(52) U.S. Cl.
CPC ......... *G16H 50/20* (2018.01); *A61B 5/14532* (2013.01); *A61B 5/486* (2013.01);
(Continued)

(58) Field of Classification Search
CPC . A61B 5/7221; A61B 5/14532; A61B 5/4866; A61B 5/7275; G16H 10/60;
(Continued)

(56) References Cited

U.S. PATENT DOCUMENTS 8,185,412 B1 * 5/2012 Harpale ................. G16H 10/60
702/19
10,341,866 B1 7/2019 Spencer et al.
(Continued)

FOREIGN PATENT DOCUMENTS

CN 101801262 A 8/2010
CN 102596307 A 7/2012
(Continued)

OTHER PUBLICATIONS

Young et al., DAMON: A Data Authenticity Monitoring System for Diabetes Management, 2018, 2018 IEEE/ACM Third International Conference on Internet-of-Things Design and Implementation (IoTDI) (Year: 2018).*
(Continued)

*Primary Examiner* — Karen A Hranek
(74) *Attorney, Agent, or Firm* — Klarquist Sparkman, LLP

(57) ABSTRACT

Systems and methods are provided for reconciling untrusted data of a subject using trusted data pertaining to the subject. Systems and methods are directed to evaluating differences in predicted data with respect to corresponding received data. Systems and methods estimate metabolic states from a combination of trusted and untrusted metabolic inputs, along with optionally using a personalized mathematical model with parameter optimization. Systems and methods provide for reconciled untrusted inputs with their measured impact of the glycemic signals that is consistent with a metabolic model. Estimation of future metabolic states for decision support and automated insulin dosing is enabled. Replay of scenarios with estimated or reconciled data is also provided.

13 Claims, 15 Drawing Sheets

(51) Int. Cl.

| | |
|---|---|
| *A61B 5/145* | (2006.01) |
| *A61M 5/172* | (2006.01) |
| *G06F 16/23* | (2019.01) |
| *G16H 10/20* | (2018.01) |
| *G16H 10/60* | (2018.01) |
| *G16H 20/13* | (2018.01) |
| *G16H 20/30* | (2018.01) |
| *G16H 20/60* | (2018.01) |
| *G16H 40/67* | (2018.01) |
| *G16H 50/20* | (2018.01) |
| *G16H 50/30* | (2018.01) |
| *G16H 50/50* | (2018.01) |
| *G16H 50/70* | (2018.01) |
| *G16H 70/20* | (2018.01) |
| *A61B 5/11* | (2006.01) |

(52) U.S. Cl.
CPC .......... *A61B 5/4866* (2013.01); *A61B 5/7221* (2013.01); *A61B 5/7275* (2013.01); *A61B 5/742* (2013.01); *A61M 5/172* (2013.01); *G06F 16/2365* (2019.01); *G16H 10/20* (2018.01); *G16H 10/60* (2018.01); *G16H 20/13* (2018.01); *G16H 20/17* (2018.01); *G16H 20/30* (2018.01); *G16H 20/60* (2018.01); *G16H 40/67* (2018.01); *G16H 50/30* (2018.01); *G16H 50/50* (2018.01); *G16H 50/70* (2018.01); *G16H 70/20* (2018.01); *A61B 5/1118* (2013.01)

(58) Field of Classification Search
CPC ........ G16H 20/17; G16H 40/67; G16H 50/50; G16H 50/70; G06F 16/2365
See application file for complete search history.

(56) References Cited

U.S. PATENT DOCUMENTS

| | | | |
|---|---|---|---|
| 11,024,429 B2 | 6/2021 | Patek et al. | |
| 2005/0192843 A1 | 9/2005 | Pratt et al. | |
| 2007/0016449 A1 | 1/2007 | Cohen et al. | |
| 2007/0033074 A1 | 2/2007 | Nitzan et al. | |
| 2007/0083335 A1 | 4/2007 | Moerman | |
| 2009/0006129 A1* | 1/2009 | Thukral | G16H 20/10 |
| | | | 705/2 |
| 2009/0069636 A1 | 3/2009 | Zivitz et al. | |
| 2010/0249561 A1 | 9/2010 | Patek et al. | |
| 2011/0098548 A1* | 4/2011 | Budiman | G16Z 99/00 |
| | | | 600/365 |
| 2011/0257893 A1 | 10/2011 | Taylor et al. | |
| 2013/0184547 A1 | 7/2013 | Taub et al. | |
| 2013/0317316 A1 | 11/2013 | Kandeel | |
| 2014/0031959 A1* | 1/2014 | Glode | G06Q 30/02 |
| | | | 700/91 |
| 2014/0095201 A1 | 4/2014 | Farooq et al. | |
| 2014/0214450 A1 | 7/2014 | Bechtold et al. | |
| 2015/0190098 A1 | 7/2015 | Patek et al. | |
| 2015/0269337 A1 | 9/2015 | Schulte et al. | |
| 2016/0342754 A1 | 11/2016 | Vettoretti et al. | |
| 2016/0354039 A1 | 12/2016 | Soto et al. | |
| 2017/0091259 A1* | 3/2017 | Curran | G06F 16/22 |
| 2017/0182248 A1 | 6/2017 | Rosinko | |
| 2017/0262604 A1 | 9/2017 | Francois | |
| 2017/0323064 A1 | 11/2017 | Bates | |
| 2018/0174675 A1* | 6/2018 | Roy | G16H 10/60 |
| 2018/0310822 A1* | 11/2018 | Indorf | A61B 5/14551 |
| 2018/0336286 A1* | 11/2018 | Shah | G06F 1/163 |
| 2019/0099555 A1 | 4/2019 | Patek et al. | |
| 2019/0173885 A1 | 6/2019 | Kamath et al. | |
| 2019/0221307 A1 | 7/2019 | Mazlish et al. | |
| 2019/0252079 A1 | 8/2019 | Constantin et al. | |
| 2019/0374137 A1 | 12/2019 | Kovatchev et al. | |
| 2020/0065681 A1* | 2/2020 | Wolf | G06N 20/00 |
| 2021/0151189 A1 | 5/2021 | Patek | |
| 2021/0151190 A1 | 5/2021 | Patek | |
| 2021/0151196 A1 | 5/2021 | Patek | |

FOREIGN PATENT DOCUMENTS

| | | |
|---|---|---|
| CN | 103907116 A | 7/2014 |
| CN | 104837517 A | 8/2015 |
| CN | 107851224 A | 3/2018 |
| EP | 4057892 A1 | 9/2022 |
| JP | 2014534483 A | 12/2014 |
| WO | 2016201120 A1 | 12/2016 |
| WO | 2021097092 A1 | 5/2021 |

OTHER PUBLICATIONS

Li et al., Resolving Conflicts in Heterogeneous Data by Truth Discovery and Source Reliability Estimation, 2014, SIGMOD'14 (Year: 2014).*

Dogan, ProTru: a provenance-based trust architecture for wireless sensor networks, Feb. 24, 2016, International Journal of Network Management (Year: 2016).*

Bleiholder et al., Conflict Handling Strategies in an Integrated Information System, 2006, Institut fur Informatik, Humboldt-Universitat zu Berlin (Year: 2006).*

Bleiholder et al., Data fusion, Jan. 2009, ACM Computing Surveys, vol. 41, Issue 1 (Year: 2009).*

International Search Report and Written Opinion dated Mar. 12, 2021 for Application No. PCT/US2000/60241 in 13 pages.

Arnolds S., et al., "Common Standards of Basal Insulin Titration in T2DM," Journal of Diabetes Science and Technology, May 2013, vol. 7, No. 3, pp. 771-788.

El Youssef J., et al., "A Review of Closed-Loop Algorithms for Glycemic Control in the Treatment of Type 1 Diabetes," Algorithms, 2009, vol. 2, pp. 518-532.

Fritzen K., et al., "Modeling of Diabetes and Its Clinical Impact," Journal of Diabetes Science and Technology, 2018, vol. 12, No. 5, pp. 976-984.

Triplitt C., "How to Initiate, Titrate, and Intensify Insulin Treatment in Type 2 Diabetes," US Pharmacist, Oct. 18, 2007, vol. 32, No. 10, pp. 10-16.

Roppenheimer: "Understanding the AndroidAPS Screens," Sep. 17, 2018, [Retrieved on May 9, 2023], XP093045426, 10 pages, Retrieved from the Internet: URL: https://github.com/roppenheimer/AndroidAPS-alt-Guide/blob/9685cf7b6e97ba5609f85fbab4fc437024f4adfb/docs/pages/Screenshots.md.

Hajizadeh I., et al., "Adaptive Personalized Multivariable Artificial Pancreas Using Plasma Insulin Estimates," Journal of Process Control, Oxford, GB, vol. 80, May 27, 2019, pp. 26-40.

* cited by examiner

100

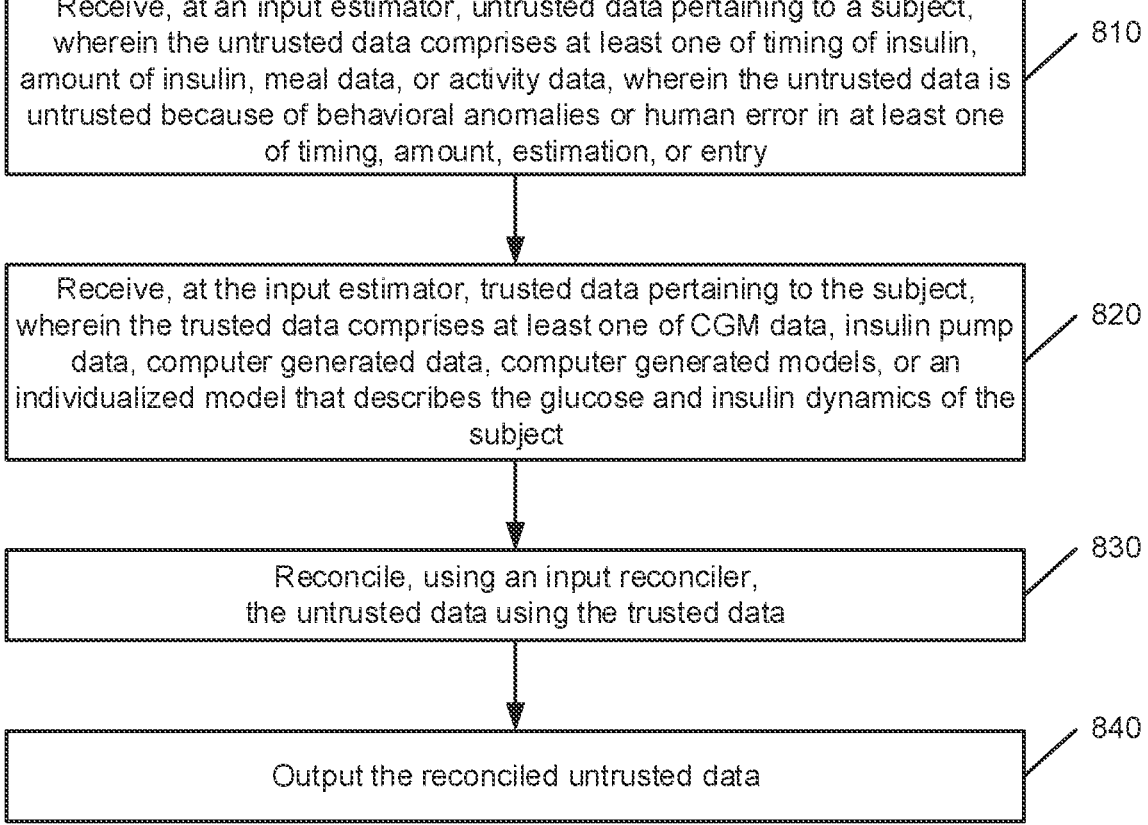

Receive, at an input estimator, untrusted data pertaining to a subject, wherein the untrusted data comprises at least one of timing of insulin, amount of insulin, meal data, or activity data, wherein the untrusted data is untrusted because of behavioral anomalies or human error in at least one of timing, amount, estimation, or entry — 810

Receive, at the input estimator, trusted data pertaining to the subject, wherein the trusted data comprises at least one of CGM data, insulin pump data, computer generated data, computer generated models, or an individualized model that describes the glucose and insulin dynamics of the subject — 820

Reconcile, using an input reconciler, the untrusted data using the trusted data — 830

Output the reconciled untrusted data — 840

Figure 9:
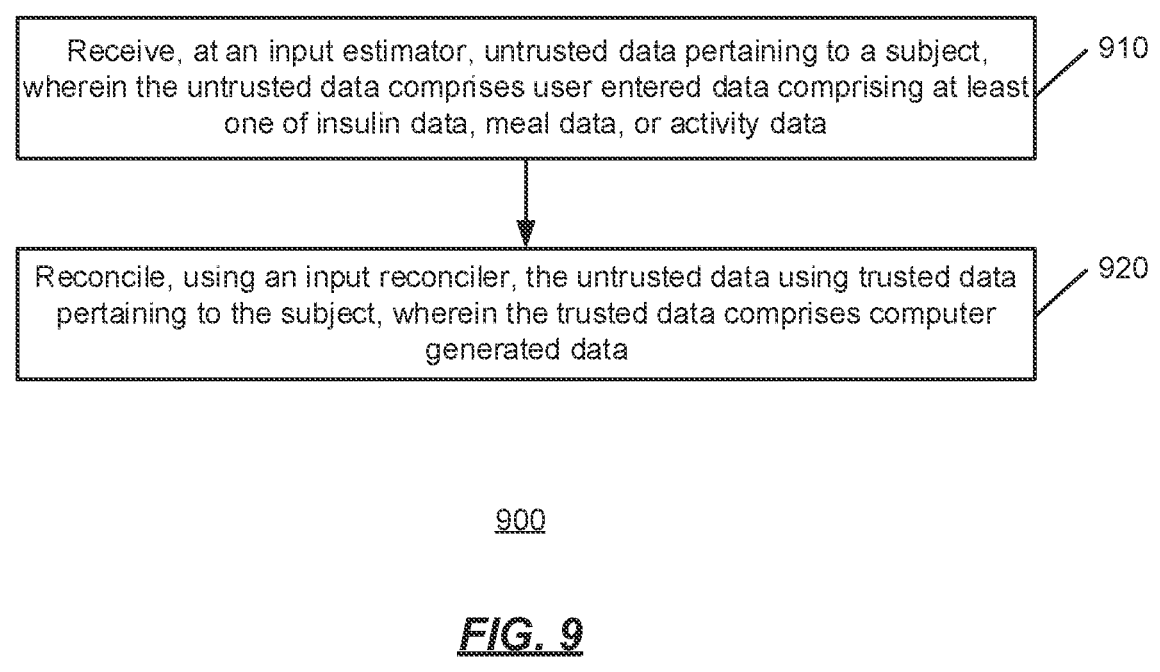

Receive, at an input estimator, untrusted data pertaining to a subject, wherein the untrusted data comprises user entered data comprising at least one of insulin data, meal data, or activity data — 910

Reconcile, using an input reconciler, the untrusted data using trusted data pertaining to the subject, wherein the trusted data comprises computer generated data — 920

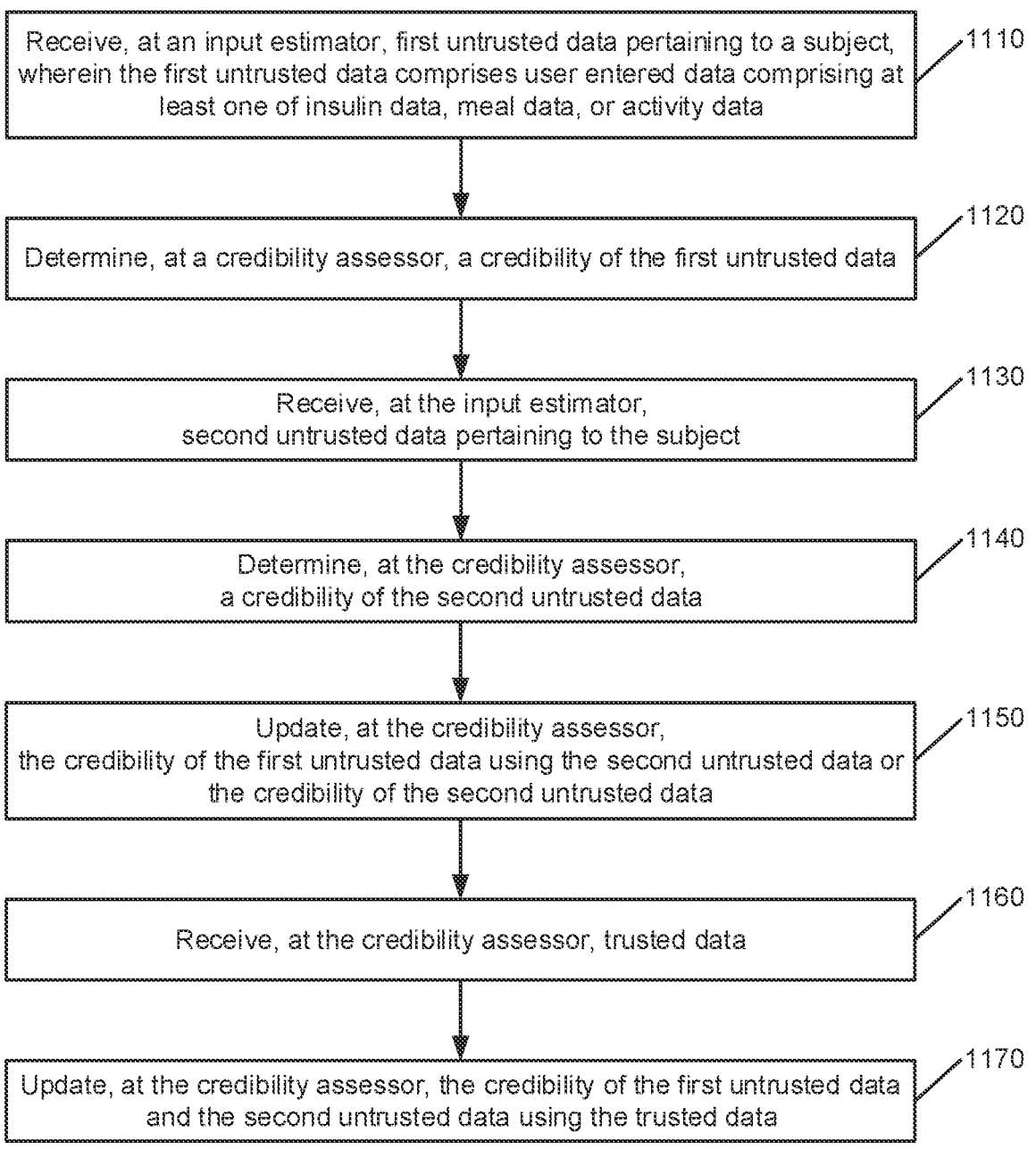

Receive, at an input estimator, first untrusted data pertaining to a subject, wherein the first untrusted data comprises user entered data comprising at least one of insulin data, meal data, or activity data — 1110

Determine, at a credibility assessor, a credibility of the first untrusted data — 1120

Receive, at the input estimator, second untrusted data pertaining to the subject — 1130

Determine, at the credibility assessor, a credibility of the second untrusted data — 1140

Update, at the credibility assessor, the credibility of the first untrusted data using the second untrusted data or the credibility of the second untrusted data — 1150

Receive, at the credibility assessor, trusted data — 1160

Update, at the credibility assessor, the credibility of the first untrusted data and the second untrusted data using the trusted data — 1170

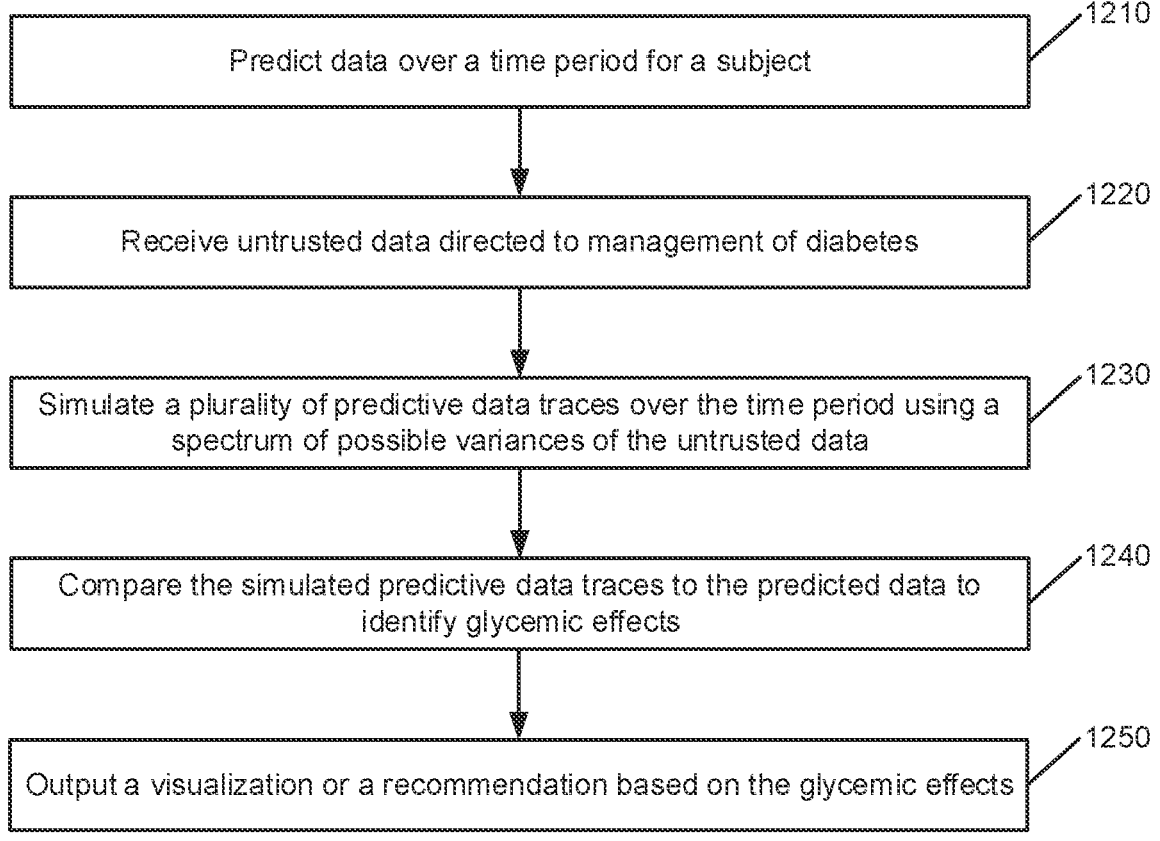

Predict data over a time period for a subject ⟋1210

Receive untrusted data directed to management of diabetes ⟋1220

Simulate a plurality of predictive data traces over the time period using a spectrum of possible variances of the untrusted data ⟋1230

Compare the simulated predictive data traces to the predicted data to identify glycemic effects ⟋1240

Output a visualization or a recommendation based on the glycemic effects ⟋1250

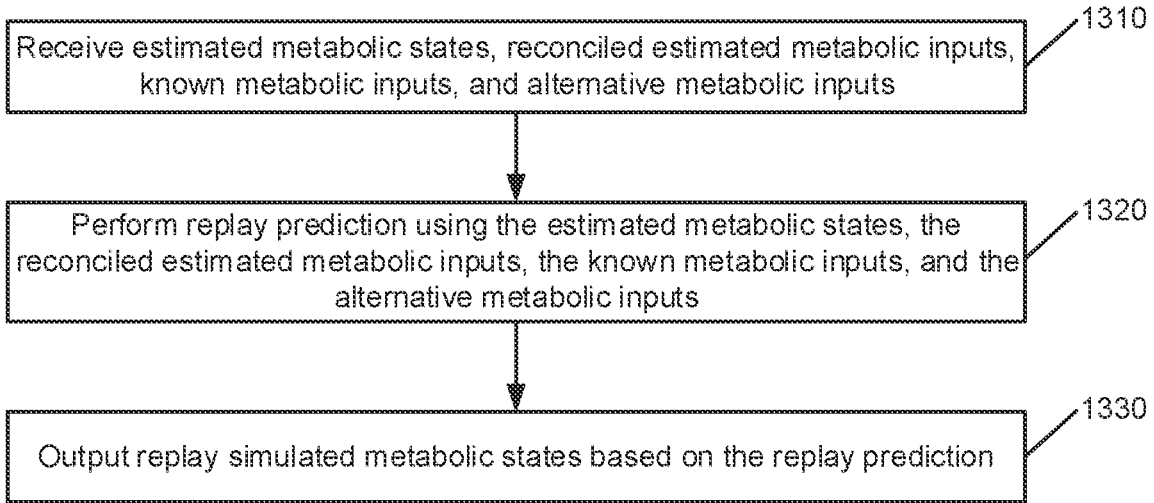

1310

Receive estimated metabolic states, reconciled estimated metabolic inputs, known metabolic inputs, and alternative metabolic inputs

1320

Perform replay prediction using the estimated metabolic states, the reconciled estimated metabolic inputs, the known metabolic inputs, and the alternative metabolic inputs

1330

Output replay simulated metabolic states based on the replay prediction

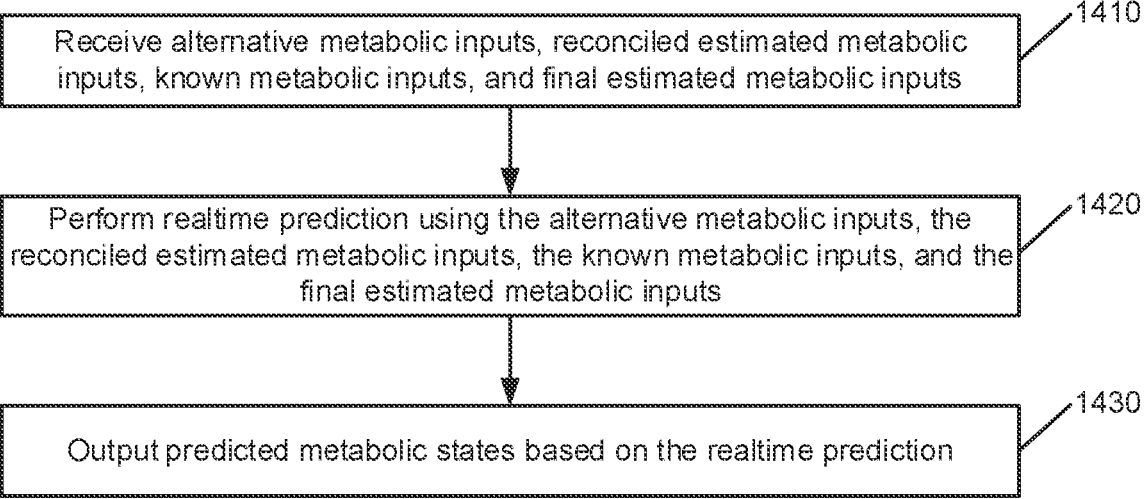

1410

Receive alternative metabolic inputs, reconciled estimated metabolic inputs, known metabolic inputs, and final estimated metabolic inputs

1420

Perform realtime prediction using the alternative metabolic inputs, the reconciled estimated metabolic inputs, the known metabolic inputs, and the final estimated metabolic inputs

1430

Output predicted metabolic states based on the realtime prediction

JOINT STATE ESTIMATION PREDICTION THAT EVALUATES DIFFERENCES IN PREDICTED VS. CORRESPONDING RECEIVED DATA

INCORPORATION BY REFERENCE TO RELATED APPLICATIONS

Any and all priority claims identified in the Application Data Sheet, or any correction thereto, are hereby incorporated by reference under 37 CFR 1.57. This application claims priority to U.S. Provisional Patent Application No. 62/935,920, filed on Nov. 15, 2019, entitled "JOINT STATE ESTIMATION PREDICTION THAT EVALUATES DIFFERENCES IN PREDICTED VS. CORRESPONDING RECEIVED DATA". The aforementioned application is incorporated by reference herein in its entirety, and is hereby expressly made a part of this specification.

BACKGROUND

With the growing adoption of CGM (continuous glucose monitoring) and connected devices, the availability and reliability of glucose time-series data has increased in recent years. However, despite the availability of reliable glucose data, accurate tracking of insulin and meal data and optimized and effective timing of meal time insulin bolusing continues to be problematic for many people with diabetes resulting in poor glucose control.

Nondiabetics have tightly controlled blood glucose (BG) values even with glucose input ranging from fasting to high carbohydrate (carb) meals and metabolic demands ranging from sleeping to intense exercise. For example, CGM data in adults without diabetes has an average glucose of 99 mg/dL and 97% time within the glycemic range of 70-140 mg/dl. This tight control results from the combined actions of glucoregulatory hormones, such as insulin, glucagon, amylin, and GLP-1 and the associated messaging between organs like the pancreas, intestine, and liver.

In contrast, blood glucose control for type 1 diabetes has historically relied on a simpler strategy of dosing insulin to cover meals and the body's baseline requirements. An example routine would have a daily dose of long-acting insulin combined with pre-meal doses of fast-acting insulin based on carb counting and self-monitored blood glucose measurements. The success of this approach relies on diligent attention and assuming the body always responds the same way to food and insulin despite all the variability of meal choice, stress, exercise and the like. As a result, most people are forced to strike a balance between avoiding the health risks of chronic high glucose and dangerous low glucose episodes.

Improved glucose control for insulin-dependent diabetes depends, in part, on a strategy that more closely mimics the way the pancreas adapts to changing metabolic conditions. One example is the artificial pancreas (AP) system.

However, patient alerts and/or alarms and pharmaceutical dosing algorithms often rely on the ability to either prospectively predict future metabolic states in real time or retrospectively simulating the physiological circumstances of life with chronic illness. In turn, predicting the future depends on the ability to estimate the current metabolic state of the patient with all available data, including data received directly from the patient (e.g., voluntary acknowledgments of meal carbohydrates) that is prone to having errors (e.g., late or completely missing meal acknowledgements with substantially underestimated carbohydrate counts). Even if algorithms predict data that is currently unavailable, if/when that predicted data is received (e.g., later from a user), there are typically differences (i.e., discrepancies). These discrepancies are currently unused, but if evaluated, can provide valuable information about the data for future use. The systems and methods described herein use and reconcile their differences.

There is a dilemma in combining human and machine inputs into a metabolic model. The most reliable inputs are machine recorded, such as those from an insulin pump or a continuous glucose monitor so it is tempting to ignore or avoid human inputs. The problem is that the glucose appearance in blood and CGM signal is delayed, even for fast acting carbohydrates. Thus, even an imperfectly announced or described meal will initially predict future glucose values better than a pre-meal CGM trace. Once the blood sugar has responded to the meal, the metabolic model can better describe the observed response. The systems and methods described herein seamlessly combine these two perspectives and reconcile their differences.

SUMMARY

According to some aspects, systems and methods are provided for reconciling untrusted data of a subject using trusted data pertaining to the subject. According to some aspects, systems and methods are directed to evaluating differences in predicted data with respect to corresponding received data.

In an implementation, a method comprises receiving, at an input estimator, untrusted data pertaining to a subject; receiving, at the input estimator, trusted data pertaining to the subject; reconciling, using an input reconciler, the untrusted data using the trusted data; and outputting the reconciled untrusted data.

Implementations may include some or all of the following features. The untrusted data comprises at least one of timing of insulin, amount of insulin, meal data, or activity data. The untrusted data is untrusted because of behavioral anomalies or human error in at least one of timing, amount, estimation, or entry. The trusted data comprises at least one of CGM data, insulin pump data, computer generated data, computer generated models, or an individualized model that describes the glucose and insulin dynamics of the subject. The method further comprises predicting a future glucose state of the subject based on the reconciled untrusted data. The untrusted data comprises reported carbs, wherein the reported carbs are unreliable or unavailable. The untrusted data comprises a stream of data inputs. The method further comprises receiving additional untrusted data and reconciling the additional untrusted data using the trusted data. The method further comprises receiving additional trusted data and reconciling the untrusted data using the additional trusted data. The method further comprises tuning an AP using the reconciled untrusted data. The method further comprises updating a behavior model of the subject using the reconciled untrusted data. The method further comprises determining that the untrusted data is unreliable or unknown. Determining that the untrusted data is unreliable or unknown comprises computing, using modeling, local variance of the untrusted data and comparing the local variance to the overall variance using the untrusted data to determine a comparison amount, wherein when the comparison amount is above a threshold, the untrusted data is determined to be unreliable or unknown. Determining that the untrusted data is unreliable or unknown comprises determining differences between the untrusted data and a model of trusted data.

Implementations may also include some or all of the following features. The method further comprises determining a credibility score for the untrusted data relative to trusted data. The method further comprises generating alerts pertaining to the subject based on the reconciled untrusted data. The method further comprises determining behavior patterns of the subject using the reconciled untrusted data. The method further comprises generating smart alerts pertaining to the subject based on the behavior patterns. The untrusted data comprises diabetes management data. The diabetes management data is estimated diabetes management data. The trusted data comprises diabetes management data corresponding to the estimated diabetes management data, wherein the diabetes management data is received from a connected device or user entry. The method further comprises comparing the untrusted data to the trusted data to identify a behavioral root cause of glycemic dysfunction.

Implementations may also include some or all of the following features. The method further comprises identifying a behavioral root cause of glycemic dysfunction using the reconciled untrusted data. The reconciling comprises: receiving the untrusted data at the input reconciler, wherein the untrusted data comprises untrusted metabolic inputs; receiving the trusted data at the input reconciler, wherein the trusted data comprises estimated untrusted metabolic inputs; and combining the untrusted data and the trusted data using a weighting function to generate reconciled untrusted metabolic inputs. The untrusted data and the trusted data received at the input reconciler are in the form of vectors, and the reconciled untrusted metabolic inputs are in the form of vectors. The weighting function is based on time-relevance. The weighting function is based on relative confidence of the untrusted data and the trusted data. The untrusted data comprises reported untrusted metabolic inputs, and the combining comprises reconciling differences between the reported untrusted metabolic inputs and the estimated untrusted metabolic inputs. The reconciling comprises making the reported untrusted metabolic inputs and the estimated untrusted metabolic inputs consistent with a behavior model. The reconciling comprises reconciling differences between the amount and timing of the untrusted metabolic inputs and the estimated untrusted metabolic inputs with measured data.

In an implementation, a method comprises receiving, at an input estimator, untrusted data pertaining to a subject, wherein the untrusted data comprises user entered data comprising at least one of insulin data, meal data, or activity data; and reconciling, using an input reconciler, the untrusted data using trusted data pertaining to the subject, wherein the trusted data comprises computer generated data.

Implementations may include some or all of the following features. The untrusted data comprises at least one of timing of insulin, amount of insulin, meal data, or activity data. The untrusted data is untrusted because of behavioral anomalies or human error in at least one of timing, amount, estimation, or entry. The trusted data comprises at least one of CGM data, insulin pump data, computer generated models, or an individualized model that describes the glucose and insulin dynamics of the subject. The method further comprises predicting a future glucose state of the subject based on the reconciled untrusted data. The untrusted data comprises reported carbs, wherein the reported carbs are unreliable or unavailable. The untrusted data comprises a stream of data inputs. The method further comprises receiving additional untrusted data and reconciling the additional untrusted data using the trusted data. The method further comprises receiving additional trusted data and reconciling the untrusted data using the additional trusted data. The method further comprises tuning an AP using the reconciled untrusted data. The method further comprises updating a behavior model of the subject using the reconciled untrusted data. The method further comprises determining that the untrusted data is unreliable or unknown. Determining that the untrusted data is unreliable or unknown comprises computing, using modeling, local variance of the untrusted data and comparing the local variance to the overall variance using the untrusted data to determine a comparison amount, wherein when the comparison amount is above a threshold, the untrusted data is determined to be unreliable or unknown. Determining that the untrusted data is unreliable or unknown comprises determining differences between the untrusted data and a model of trusted data. The method further comprises determining a credibility score for the untrusted data relative to trusted data. The method further comprises generating alerts pertaining to the subject based on the reconciled untrusted data. The method further comprises determining behavior patterns of the subject using the reconciled untrusted data. The method further comprises generating smart alerts pertaining to the subject based on the behavior patterns.

Implementations may also include some or all of the following features. The untrusted data comprises diabetes management data. The diabetes management data is estimated diabetes management data. The trusted data comprises diabetes management data corresponding to the estimated diabetes management data, wherein the diabetes management data is received from a connected device or user entry. The method further comprises comparing the untrusted data to the trusted data to identify a behavioral root cause of glycemic dysfunction. The method further comprises identifying a behavioral root cause of glycemic dysfunction using the reconciled untrusted data. The reconciling comprises: receiving the untrusted data at the input reconciler, wherein the untrusted data comprises untrusted metabolic inputs; receiving the trusted data at the input reconciler, wherein the trusted data comprises estimated untrusted metabolic inputs; and combining the untrusted data and the trusted data using a weighting function to generate reconciled untrusted metabolic inputs. The untrusted data and the trusted data received at the input reconciler are in the form of vectors, and the reconciled untrusted metabolic inputs are in the form of vectors. The weighting function is based on time-relevance. The weighting function is based on relative confidence of the untrusted data and the trusted data. The untrusted data comprises reported untrusted metabolic inputs, and the combining comprises reconciling differences between the reported untrusted metabolic inputs and the estimated untrusted metabolic inputs. The reconciling comprises making the reported untrusted metabolic inputs and the estimated untrusted metabolic inputs consistent with a behavior model. The reconciling comprises reconciling differences between the amount and timing of the untrusted metabolic inputs and the estimated untrusted metabolic inputs with measured data. The method further comprises performing replay prediction using the reconciled untrusted data and the trusted data. The method further comprises outputting simulated metabolic states based on the replay prediction. The method further comprises performing real time prediction using the reconciled untrusted data and the trusted data. The method further comprises outputting simulated metabolic states based on the real time prediction.

In an implementation, a method comprises predicting data over a time period for a subject; receiving untrusted data directed to management of diabetes; simulating a plurality of predictive data traces over the time period using a spectrum of possible variances of the untrusted data; comparing the simulated predictive data traces to the predicted data to identify glycemic effects; and outputting a visualization or a recommendation based on the glycemic effects.

Implementations may include some or all of the following features. The untrusted data comprises glucose data, and the predictive data traces comprise predictive glucose traces. Predicting the glucose data is based on trusted CGM data and an individualized model of the glucose-insulin kinetics of the subject. Predicting the glucose data comprises providing a best estimate glucose trace representing glucose state over time. The untrusted data directed to management of diabetes comprises at least one of a timing of insulin, an amount of insulin, meal data, or activity data. The glycemic effects are associated with differences in at least one of an amount of diabetes management data or a timing of diabetes management data.

In an implementation, a system comprises a processor and a metabolic model, wherein the processor is configured to receive untrusted user inputs and reconcile the untrusted user inputs with trusted inputs using the metabolic model.

Implementations may include some or all of the following features. The processor is further configured to optimize the predictive ability of the metabolic model to predict future glucose levels. The processor is further configured to allow a replay of events and outcomes with alternate treatment procedures. The processor is further configured to provide real time prediction of future metabolic states. The processor is further configured to determine the credibility of the untrusted user inputs. The processor is further configured to provide a score corresponding the credibility. The processor is further configured to perform a replay analysis directed to at least one replay application. The at least one replay application comprises assessment of blood glucose (BG) outcome metrics in the analysis, identification of credible instances of scenarios in the replay analysis, evaluation of data quality, credibility profiles, and data credibility as a function of time of day. The processor is further configured to perform a reconciled projection directed to at least one real time application. The at least one real time application comprises confidence of medical actions and determination of need to wait before providing advice.

Implementations may also include some or all of the following features. The untrusted user inputs comprise estimated carbs. The untrusted user inputs comprise a time series of uncertain metabolic inputs. The trusted inputs comprise CGM and insulin pump readings. The trusted inputs comprise a time series of trusted metabolic inputs. The processor is further configured to output estimated metabolic states in time series form, final reconciled estimated metabolic states in time series form, and credibility of final estimated metabolic states and reconciled estimated inputs in time series form. The processor is comprised within a joint state/input estimator, and the metabolic model is a plugin.

In an implementation, a method comprises receiving, at an input estimator, untrusted data pertaining to a subject, wherein the untrusted data comprises user entered data comprising at least one of insulin data, meal data, or activity data; determining, at a credibility assessor, a credibility of the untrusted data; receiving trusted data at the credibility assessor; and updating, at the credibility assessor, the credibility of the untrusted data using the trusted data.

Implementations may include some or all of the following features. Determining the credibility of the untrusted data comprises: determining a first credibility based on at least one of a lack of completeness of the untrusted data or a lack of continuity of the untrusted data; determining a second credibility based on expected behaviors indicative of at least one of the lack of completeness of the untrusted data or the lack of continuity of the untrusted data; determining a third credibility based on artifacts in estimated inputs indicative of systemic unknown factors; and aggregating the first credibility, the second credibility, and the third credibility. Determining the first credibility comprises using measured signals as an input, determining the second credibility comprises using the untrusted data and trusted data as inputs, and determining the third credibility comprises using the untrusted data, estimated untrusted data, and reconciled data as inputs.

In an implementation, a method comprises receiving, at an input estimator, first untrusted data pertaining to a subject, wherein the first untrusted data comprises user entered data comprising at least one of insulin data, meal data, or activity data; determining, at a credibility assessor, a credibility of the first untrusted data; receiving, at the input estimator, second untrusted data pertaining to the subject; determining, at a credibility assessor, a credibility of the second untrusted data; updating, at the credibility assessor, the credibility of the first untrusted data using the second untrusted data or the credibility of the second untrusted data; receiving trusted data at the credibility assessor; and updating, at the credibility assessor, the credibility of the first untrusted data and the second untrusted data using the trusted data.

Implementations may include some or all of the following features. Determining the first credibility of the untrusted data comprises: determining a first credibility based on at least one of a lack of completeness of the untrusted data or a lack of continuity of the untrusted data; determining a second credibility based on expected behaviors indicative of at least one of the lack of completeness of the untrusted data or the lack of continuity of the untrusted data; determining a third credibility based on artifacts in estimated inputs indicative of systemic unknown factors; and aggregating the first credibility, the second credibility, and the third credibility. Determining the first credibility comprises using measured signals as an input, determining the second credibility comprises using the untrusted data and trusted data as inputs, and determining the third credibility comprises using the untrusted data, estimated untrusted data, and reconciled data as inputs.

In an implementation, a method comprises receiving estimated metabolic states, reconciled estimated untrusted metabolic inputs, trusted metabolic inputs, and alternative metabolic inputs; performing replay prediction using the estimated metabolic states, the reconciled estimated untrusted metabolic inputs, the trusted metabolic inputs, and the alternative metabolic inputs; and outputting replay simulated metabolic states based on the replay prediction.

Implementations may include some or all of the following features. The estimated metabolic states, the reconciled estimated untrusted metabolic inputs, and the trusted metabolic inputs each comprise a time series. Performing the replay prediction comprises estimating metabolic states for a duration of the time series for the estimated metabolic states, the reconciled estimated untrusted metabolic inputs, and the trusted metabolic inputs to generate the replay simulated metabolic states.

In an implementation, a method comprises receiving alternative metabolic inputs, reconciled estimated untrusted metabolic inputs, trusted metabolic inputs, and final estimated metabolic inputs; performing real time prediction using the alternative metabolic inputs, the reconciled estimated untrusted metabolic inputs, the trusted metabolic inputs, and the final estimated metabolic inputs; and outputting predicted metabolic states based on the real time prediction.

Implementations may include some or all of the following features. Performing the real time prediction comprises: extrapolating time series for the reconciled estimated untrusted metabolic inputs and the trusted metabolic inputs; and estimating metabolic states into the future using the extrapolated time series, the alternative metabolic inputs, and the final estimated metabolic states. The method further comprises filtering the extrapolated time series to prevent jitter in the predicted metabolic states. The estimated metabolic states are in time series form. The method further comprises filtering the estimated metabolic states to generate the predicted metabolic states. The estimating the metabolic states uses a behavior model of a subject. Extrapolating the time series uses weighting of historical data based on at least one of a time of day, features of a current estimated state, or a database of past metabolic inputs.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings:

FIG. 8 is an operational flow of an implementation of a method for reconciling data;

FIG. 9 is an operational flow of another implementation of a method for reconciling data;

FIG. 11 is an operational flow of another implementation of a method for determining the credibility of data;

FIG. 12 is an operational flow of an implementation of a method for using untrusted data to provide output based on glycemic effects;

FIG. 13 is an operational flow of an implementation of a method for using replay prediction;

FIG. 14 is an operational flow of an implementation of a method for using real time prediction.

DETAILED DESCRIPTION

Figure 1:
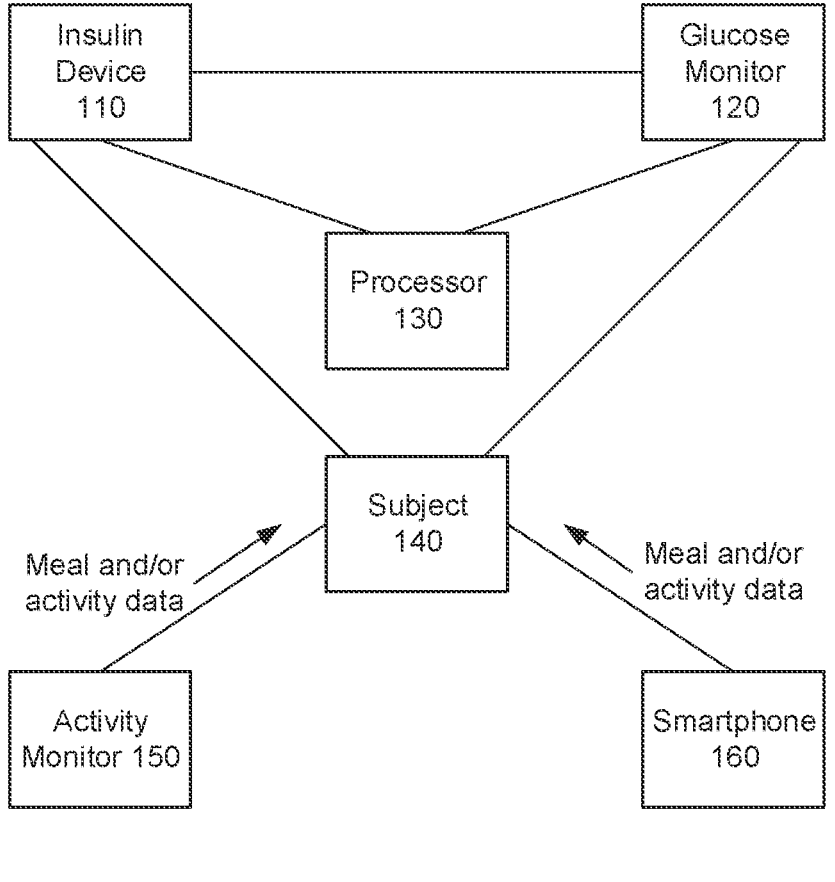
FIG. 1 is an illustration of an exemplary environment for evaluating and visualizing differences in data.

The claimed subject matter is described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

The description is not to be taken in a limiting sense, but is made merely for the purpose of illustrating the general principles of the invention, since the scope of the invention is best defined by the appended claims.

Various inventive features are described herein that can each be used independently of one another or in combination with other features.

Unmeasured human behaviors and untrustworthy reporting of relevant metabolic events (e.g., meals and boluses) are much more impactful than the effects of sensor error on inferences from signal processing of glucose time series data. Consequently, untrusted data can be reconciled with trusted data, providing reconciled untrusted and trusted data as estimated metabolic data useful for prediction or replay of glucose time series data.

In some aspects, systems and methods are provided for reconciling untrusted data of a subject using trusted data pertaining to the subject. In some aspects, systems and methods are directed to evaluating differences in predicted data with respect to corresponding received data.

As described further herein, a retrospective prediction function evaluates if other insulin dosing strategies for the same meal would have better outcomes (e.g., lower glycemic risk). The retrospective prediction function takes the initial (e.g., premeal) state of the patient, one or more meal events, and an insulin dosing strategy as inputs and then maps it to the resulting glucose excursions for that meal/day. In some implementations, the retrospective prediction function: (1) maps the original data (e.g., meal and insulin) to the observations (e.g., CGM) with a sufficient (e.g., predetermined) degree of accuracy, (2) maps alternate dosing strategies to the resulting glucose excursions in manner that models the patient's (the patient is also referred to herein as "the subject") physiology (e.g., insulin activity and carbohydrate sensitivity), and (3) provides reliable and interpretable solutions to the problem such as an estimate of insulin on board that is a stable and smooth function. Joint state estimator and meal estimation systems and methods herein combine known inputs and user-announced meals to solve for this function. The output of is a function that can replay alternate insulin strategies with the same inputs' states (or the results of the alternate insulin strategies themselves).

In an implementation, the replay function may be constructed from the same data set using other approaches known to one skilled in the art of metabolic models. One example approach would be to fit the parameters of a known metabolic model to the patient's data or a clinical study. Another possible approach would be to train a neural network with similar data to predict the glucose excursions.

FIG. 1 is an illustration of an exemplary environment 100 for evaluating and visualizing differences in data. The environment comprises an insulin device 110, a glucose monitor 120, a processor 130, a subject 140, an activity monitor 150, and a smartphone 160.

One or more of the insulin device 110, the glucose monitor 120, the processor 130, the activity monitor 150, and the smartphone 160 may be in communication through a network. The network may be a variety of network types including the public switched telephone network (PSTN), a cellular telephone network, and a packet switched network (e.g., the Internet). Although only insulin device 110, one glucose monitor 120, one processor 130, one subject 140, one activity monitor 150, and one smartphone 160 are shown in FIG. 1, there is no limit to the number of insulin devices 110, glucose monitors 120, processors 130, subjects 140, activity monitors 150, and smartphones 160 that may be supported.

The insulin device 110 may be any device that dispenses insulin, such as syringes, pumps (e.g., external, mechanical, patch, or implanted), and inhalers, for example. The insulin device 110 may also include devices that dispense other drugs that help control glucose levels like glucagon (dual-hormone artificial pancreas), GLP-1, etc.

The glucose monitor 120 may be any type of CGM or SMBG (self-monitoring of blood glucose) device, depending on the implementation. The glucose monitor 120 may be a connected device that provides glucose readings continuously or provides a set of glucose readings when the device is scanned or downloaded. In addition to glucose readings, the glucose monitor 120 may record user interactions such as when and how a user (e.g., a subject, a patient, a caregiver, a medical professional, etc.) views their glucose traces and how they respond to alerts and alarms. The user interaction can provide insights into the timing and motivation of treatment decisions including why and when they are considering the effects of eating or dosing insulin.

The processor 130 collects data from the insulin device 110 and the glucose monitor 120 and the subject 140 and runs methods described herein. To have a robust system, these calculations may be dynamic and distributed depending on which devices and processors are connected. For example, cloud computing may be used when there is connectivity, a smartphone processor may be used when there is no connectivity and then a transmitter or a smartwatch may be used when the smartphone is not connected. Complex calculations, like model optimization, may only run when more powerful processors are available. When powerful processors are not available, algorithms may use the most recent parameters or simpler approximations.

Figure 15:
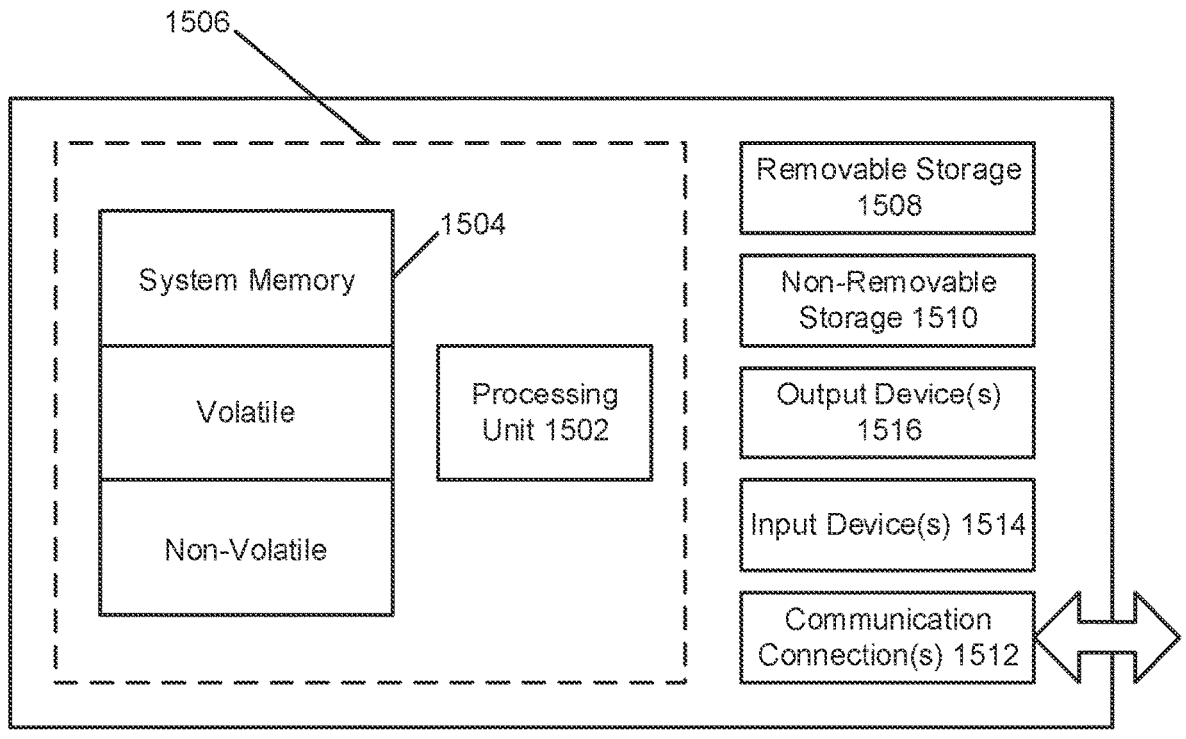
FIG. 15 shows an exemplary computing environment in which example embodiments and aspects may be implemented.

The processor 130 (as well as the insulin device 110, the glucose monitor 120, the activity monitor 150, and/or the smartphone 160) may be implemented using a variety of computing devices such as smartphones, desktop computers, laptop computers, and tablets, for example. Other types of computing devices may be supported. A suitable computing device is illustrated in FIG. 15 as the computing device 1500.

The subject 140 can provide inputs to the system including information about meals, activity, and diabetes treatments using e.g., any computing device that is in communication with the system, such as the smartphone 160 or other computing device of the subject 140. These inputs can be user-initiated or prompted by the system. These inputs can describe current, previous, and/or upcoming events.

The activity monitor 150 may be any device that monitors the user's physiologic and mental state. One example is a fitness tracker that monitors activity, exercise, and sleep with accelerometers, gyroscopes, heart rate, and oxygen sensors.

This can also include smartphones as they can detect location and user activity/interactions, or a smart home device (e.g., Amazon Alexa). In some implementations, the activity monitor 150 includes devices that detect meals.

The smartphone 160 can be used as an activity and context monitor, data entry device, data collection (talking to devices with Bluetooth, NFC, Wi-Fi, etc.) and run applications (e.g., apps) that estimate nutritional information through manual entry or automated entry (e.g., photos).

The systems and methods described herein estimate metabolic states from a combination of trusted and untrusted metabolic inputs, along with optionally using a personalized mathematical model with parameter optimization. Systems and methods provide for reconciled untrusted inputs with their measured impact of the glycemic signals (using CGM) that is consistent with the metabolic model (optional). Estimation of future metabolic states for decision support and automated insulin dosing is enabled with the systems and methods described herein. Credibility of the data, for example, rather than declaring whole days as being valid or invalid, and providing a time series of credibility data alongside the metabolic state estimates avoids problems to modeling a continuous process such as overnight predictions. Replay of scenarios with estimated or reconciled data is also provided. All data, including metabolic states (trusted and untrusted reconciled), along with corresponding credibility, prediction and replay are provided in a time-domain perspective. Retrospective predictions, also referred to as replay compiling, and prospective prediction, also referred to real time prediction compiling, are made more reliable and accurate by the reconciliation process(es) of implementations described herein.

Figure 2:
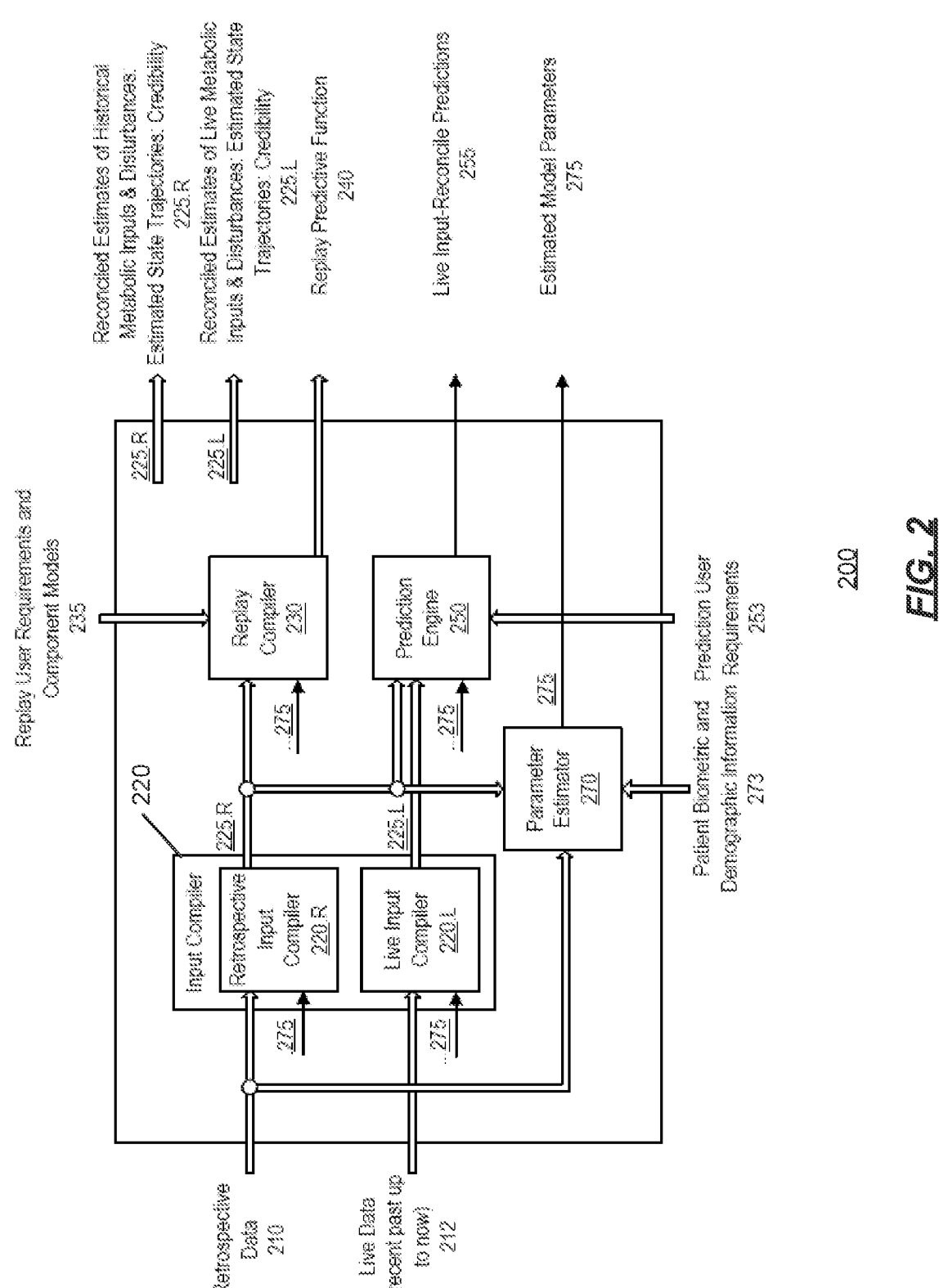
FIG. 2 is a block diagram of an implementation of a diabetes management processing platform.

FIG. 2 is a block diagram of an implementation of a diabetes management processing platform 200. The platform 200 uses reconciliation, replay analysis, prediction and/or credibility determination together with an optional optimization of parameters to predict future analyte values or unobserved states, inform bolus decisions, assess carbs on board, assess insulin on board, enable smart alert functionality, deliver retrospective therapy optimization, and to provide feedback to estimation, for example. The diabetes management platform 200 includes inputs, outputs, and interrelationships of the modules, are described further herein.

The platform 200 comprises an input compiler 220, a replay compiler 230, a prediction engine 250, and a parameter estimator 270. The input compiler 220 comprises a retrospective input compiler 220R and a live input compiler 220L. The platform 200 may comprise more or fewer modules depending on the implementation. In some implementations, for example, the parameter estimator 270 is optional.

Data is provided to the input compiler 220 and may include measured signals, indirectly observed metabolic inputs that are trustworthy (i.e., trusted metabolic inputs), indirectly observed metabolic inputs that are not trustworthy (i.e., untrusted metabolic inputs), along with an estimated initial state that describes the condition of the patient at the time of the first data point. Examples of measured signals include blood glucose data from a blood glucose monitor (BGM) or a continuous glucose monitor or insulin delivery data from a connected insulin pen or an insulin pump. Examples of trusted metabolic inputs include reports of meal activity or physical activity from professional caregivers in a clinical setting with assurances of accuracy in terms of timing, degree, and content. Examples of untrusted metabolic inputs include reports of meal activity or physical activity in the field using pencil/paper (e.g., handwritten) diaries or logging functions of medical devices that have no means of enforcing accuracy.

The input compiler 220 processes retrospective data 210 using the retrospective input compiler 220R and processes live data 212 using the live input compiler 220L. Retrospective data 210 is provided to the retrospective input compiler 220R and the parameter estimator 270 and is further described with respect to FIG. 3 and FIG. 9 for example. Live data 212 is provided to the live input compiler 220L. Live data 212 is real time or within a particular time window or during a processing cycle or the like, depending on the implementation. Live data 212 is further described with respect to FIG. 6 and FIG. 9 for example.

In an implementation, the input compiler 220 comprises a state estimator (e.g., the state estimator 340 shown in FIGS. 3 and 6), which may use an individualized physiological model to produce outputs such as reconciled estimated metabolic inputs, estimated metabolic states of the patient for the duration of the input data, a numerical assessment of the credibility of the estimated states and, and a numerical assessment of the credibility of the reconciled estimated metabolic inputs. The reconciled estimated metabolic inputs are used along with their linkage to the assessment of the credibility of the estimated metabolic states and the credibility of the reconciled estimated metabolic inputs. In addition to their use within the interrelated modules of the system, the reconciled data, such as reconciled meal and insulin histories can be reported back out to the patient or other user.

The replay compiler 230 uses the output 225R of the input compiler 220 operating on retrospective data 210 (i.e., the output 225R of the retrospective input compiler 220R), along with a state estimator using estimated model parameters 275, which may be an individualized physiological model, and replay user requirements and component models 235, to produce output such as replay predictive function 240 and/or other replay analysis. The replay predictive function 240 may operate on alternative metabolic inputs (different from the reconciled metabolic inputs), either in the form of alternative specific inputs or in the form of alternative strategies, to produce a replay prediction in the form of a trajectory of simulated metabolic outcomes from the alternative metabolic inputs along with the credibility of the associated predictions. The resulting replay predictive function 240 can be used in a wide variety of applications, including retrospective therapy optimization or retrospective insights about therapy. The assessment of credibility of the replay prediction is directly linked to the credibility of the reconciled estimated metabolic inputs, both of which enable further features and functions described herein. Additional applications and outputs of the replay compiler include basal titration, illustrating the impact of bolus timing vs. meal timing, and validation of AP algorithms, for example.

The prediction engine 250 uses the output 225L of the live input compiler 220L operating on live data 212, along with a state estimator using estimated model parameters 275, which may be an individualized physiological model, and prediction user requirements 253, to produce live input-reconcile predictions 255. The live input-reconcile predictions 255 operate on candidate present and future metabolic inputs to produce a real time prediction in the form of a predicted trajectory of metabolic outcomes for the candidate inputs along with the credibility of the associated predictions. The live input-reconcile predictions 255 can be used in a wide variety of applications including comparing alternative actions for (i) real time decision-making, including selection of the next control step in closed-loop control of diabetes, predictive bolus advisors, and decision support, and (ii) for producing real time insights, such as smart alerts. The assessment of credibility of the live input-reconcile predictions 255 is directly linked to the credibility of the reconciled estimated metabolic inputs, both of which enable further features and functions described herein.

The parameter estimator 270 uses patient biometric and demographic information 273 along with the retrospective data 210 and the output 225R of the retrospective input compiler 220R to determine and output estimated model parameters 275 (e.g., of the state estimator, which may be an individualized physiological model). An individualized physiological model is helpful, but not required in implementations. The parameter estimator 270 is useful in the context of implementations that utilize an individualized model for estimation but is not critical required.

Figure 3:
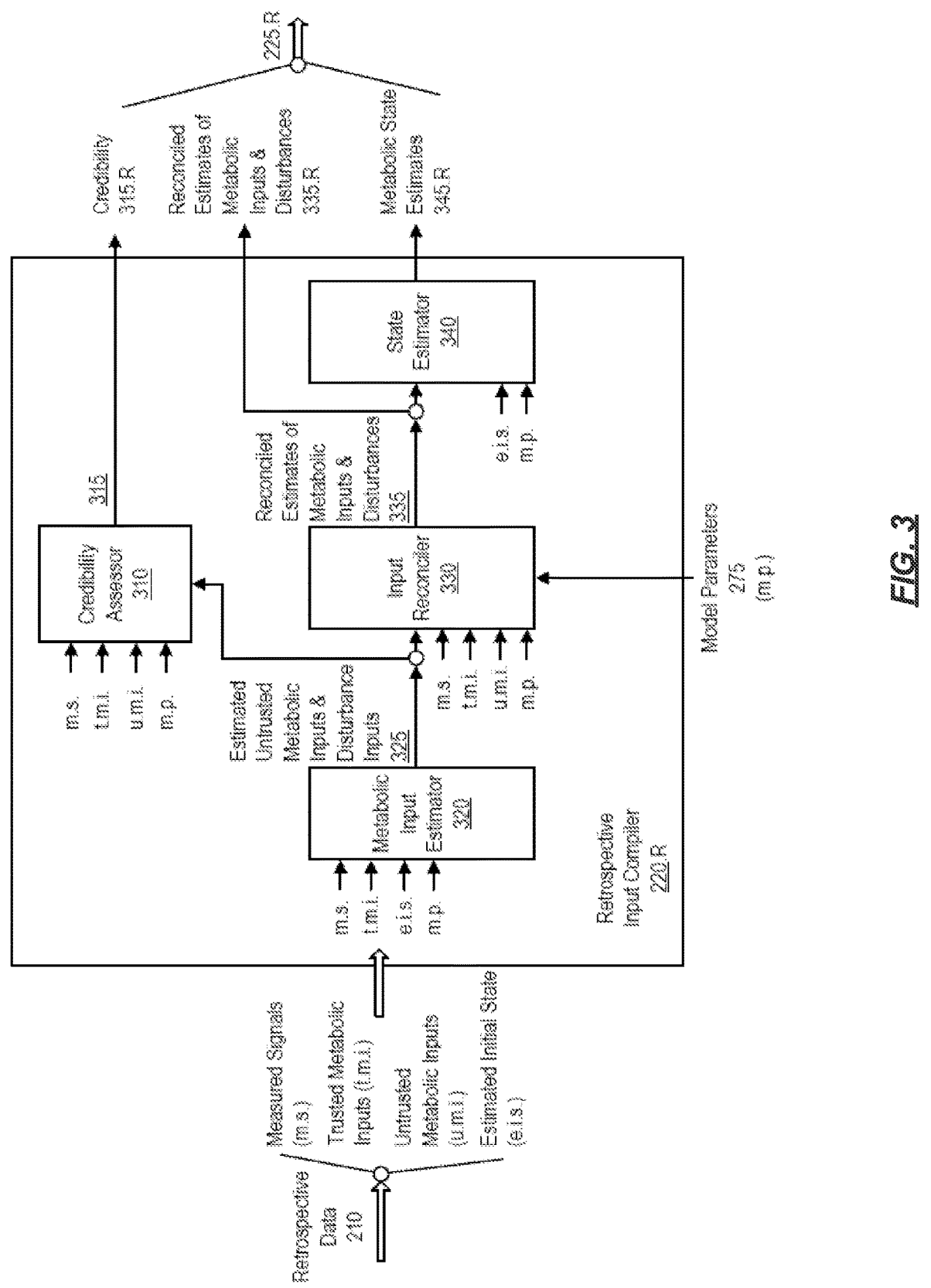
FIG. 3 is a block diagram of an implementation of a retrospective input compiler.

FIG. 3 is a block diagram of an implementation of a retrospective input compiler 220R. Broadly, this approach to combining trusted and untrusted metabolic inputs can be applied any time data inputs with uncertain accuracy or reliability are sought to be reconciled. The retrospective input compiler 220R comprises a metabolic input estimator 320, a credibility assessor 310, an input reconciler 330, and a state estimator 340.

As described with respect to FIG. 2, retrospective data 210 is input to the retrospective input compiler 220R. Retrospective data may come in a variety of formats, including measured signals or inputs, trusted metabolic inputs, untrusted metabolic inputs, and estimated state(s). In the retrospective input compiler 220R, the inputs are classified as trusted or untrusted, and various estimates are determined, and estimates of the untrusted inputs in the form of reconciled estimates of historical metabolic inputs are calculated, e.g., taking an unacknowledged estimate of carbohydrates and reconciling with received data.

The measured signals are comprised within the retrospective data 210 and provided as input to the retrospective input compiler 220R, and more particularly to a metabolic input estimator 320. The measured signals are typically measurements of glucose levels including, for example, real time CGM readings, confidence readings assigned to the CGM values, self-monitoring blood glucose readings (blood glucose meter), and/or retrospectively calibrated or corrected CGM readings and other measure signals, such as insulin measured by an internal insulin sensor.

Metabolic inputs are comprised within the retrospective data 210 and provided as input to the retrospective input compiler 220R, and more particularly to a metabolic input estimator 320. Metabolic inputs can be generally thought of in terms of what happened and when (timing and magnitude). An example may include estimating metabolic state from known metabolic inputs recorded by an insulin pump and uncertain metabolic inputs describing a meal recorded by the user.

Trusted metabolic inputs are the known metabolic inputs, which may be recorded directly by an electronic/electromechanical device and/or estimated by a machine. Examples include insulin pumps and connected insulin pens that record the insulin injection time. These devices directly measure the action of the pump or syringe that is dispensing insulin with a high degree of accuracy. Note there can still be faults, like occlusions, that cause uncertain infusion rates. Regarding insulin inputs, the systems and methods contemplated herein are not tied to a specific model for delivery (e.g., pump versus pen).

Untrusted metabolic inputs are uncertain metabolic inputs, which may be entered by the user. Uncertain inputs can be thought of in terms of what happened and when (e.g., timing and magnitude). An example is a user input providing a meal's carbohydrate content and meal time that is manually entered on a phone app. More broadly, it includes any input to the time series that relies on user entry that is not confirmed by a connected device, such as insulin dosing with a nonconnected pen or pump. This may include the case of carbohydrates estimated by another phone app, e.g., ByteSnap. In principle, untrusted metabolic inputs could also be the unreliable action of insulin due to infusion pump and infusion site variability. This is the uncertainty around these dynamic inputs to the system that may be reconciled with retrospective measurements (like CGM). The untrusted can refer to inexact timing or content of the event data, such as for meal entry. Untrusted metabolic inputs can also include factors like exercise or illness that are difficult for the user to quantify. There are also untrusted metabolic inputs that result from indirectly measured inputs.

The meal input is defined in terms of time and amount of carbohydrates. User inputs (meal announcements) are typically defined as a single carbohydrate event. Some exemplary user-entered meal data that may be untrusted include: user is estimating the amount of carbs or other nutrient information about a meal, e.g., user may estimate for a burrito but not include chips and salsa eaten while waiting; a meal is simplified to a small-medium-large qualifier; a meal is simplified to an amount of carbohydrates that does not account for the glycemic index; meal response also depends on fat and protein content; user is anticipating when they are going to eat when they are entering a premeal bolus; user is prompted to recalling when they ate after the system has detected a meal response; and system records a single time for the meal that spans a period including appetizers, main course, and dessert.

Some examples of untrusted metabolic inputs that result from indirectly measured inputs include: meal apps that estimate carbs using databases, barcodes, restaurant photos etc.; meal apps that categorize the upcoming meal from a library of previous meals; exercise intensity and duration estimated from a fitness tracker (heart rate/accelerometer); and sleep duration estimated from a fitness tracker.

Table 1 shows examples of metabolic inputs with known input and uncertain input.

TABLE 1

| Metabolic Input | Known Input | Uncertain Input |
|---|---|---|
| 'Simple' Meal (time and carb content) | Manual logging of data in a clinical context | User entered time and size or carb estimate Carb acknowledgement |
| Meal type (Carb/ protein/fat/etc.) | Provided meals (like diet company meal) | Photo tools Nutritional database |
| Insulin injection | Connected pen | User entered time, type and amount Uncertainty of pen priming |
| Insulin pump | Pump | n/a |
| Oral meds | n/a | User entered/confirmed |
| Glucagon | Dual hormone pump | User injection |
| Exercise | Controlled variable | Fitness tracker, heart rate |
| Sleep | Controlled variable | Fitness tracker |
| Insulin delivery | | Pump occlusion Variable time curves |

The last row in Table 1 contemplates including the "unreliable action" of insulin due to infusion pump and infusion site variability. In other words, the pump reliably records the plunger moving but due to problems with the infusion site or catheter this insulin may not be entering the body. As a result, the amount of insulin pumped would need to be reconciled with the observed (lack of) insulin action, in some implementations.

Other inputs may include gut and glucose rate of appearance, sensor lag, and could be expanded to general metabolites, for example.

Estimated initial state(s) are data comprised within the retrospective data 210 and provided as input to the retrospective input compiler 220R, and more particularly to a metabolic input estimator 320. The estimated initial state provides an initial state of the glycemic model, including glucose levels (blood and other compartments), insulin levels (blood and other compartments), carbohydrate levels (due to previously eaten meal), and metabolic demands (effects of previous exercise and current activity level). This may be a vector as it defines these quantities at one point in time (the initial state).

In some embodiments, one or more model parameters 275 may be provided as inputs to the retrospective input compiler 220R (e.g., to the input reconciler 330).

The output of the retrospective input compiler 220R comprises (i) reconciled estimated metabolic inputs (including both trusted and untrusted inputs), (ii) a corresponding estimate of the metabolic state, and (iii) assessments of credibility of the input and state estimates.

More particularly, the metabolic input estimator 320 receives and processes the retrospective data 210 and generates (outputs) estimated untrusted metabolic inputs and disturbance inputs 325.

The metabolic input estimator 320 may use an individual mathematical model that is a compartmental model of the metabolic processes that produce or consume glucose in the body. For example, this model has terms that describe the increase in glucose following meals and the uptake of this glucose into muscles and adipose tissue that is stimulated by insulin. The model is individualized to account for between-subject differences in the insulin action and meal metabolism and diabetes (e.g., type 1 versus type 2).

In one implementation, the systems and methods described herein estimate the time series of uncertain metabolic inputs and the states themselves, which may include estimates unknown/incompletely observed events. In this implementation, metabolic input estimation is based on the measured signals, past estimated metabolic states and known metabolic inputs, which are extracted to form vectors of measurements, inputs and corresponding initial state. Uncertain inputs (e.g., reported meals) are not inputs at this stage. Only what was known in the past and what was measured is inputted. Raw inputs are converted into vectors of appropriate length, that depends on the use (e.g., real time 6 hours versus retrospective using an extended day of 36 hours to get a full daily cycle and avoid edge effects/ boundary conditions). These are measured signals. The range of data (time span) depends on the application (i.e., the implementation) and may range from minutes to hours to days. The data may then aligned, snapped, interpolated and smoothed as needed depending on the implementation. Next, the system uses a linear dynamic model (e.g., without mapping) to determine the systematic residual, which is the difference between the measure signals and the model predicted impact of the estimated initial metabolic state and the known metabolic inputs. The unknown inputs that optimally explain the systematic residual are then computed based on the fit of the systematic residual and the shape of the estimated unknown inputs (e.g., regularization). For example, the set penalties for the fit, emphasizing (i) high confidence samples, (ii) last samples, (iii) last rate of change, (iv) important samples (e.g., hypoglycemia or hyperglycemia) and the set regularization penalties to achieve desirable properties may include (i) smoothness or discreteness of the estimated unknown input, (ii) allowing/disallowing bias, (iii) allowing/disallowing high rates of change or acceleration (other set constraints can include specifying non-negativity (e.g., for meals)). This type of inverse problem that is solved by regularized deconvolution. A challenge is constraining the inversion to physically reasonable and interpretable values that are reasonably consistent with the measured results (CGM traces), initial conditions and provided inputs. As such constraints may be imposed, including non-negative meals, regularization of episodic meals and slowly time-varying insulin differential to achieve desirable properties, dynamically adjusting the importance of fitting the data based on quality, for example, may be performed. From these computations, vectors of both estimated metabolic state trajectory may be extracted and raw estimated uncertain metabolic inputs are extracted.

The credibility assessor 310 generates an output of credibility 315R (outputs a credibility value). The credibility 315R is derived from the difference between the raw estimates of the untrusted inputs and what is reported.

The credibility assessor 310 evaluates a plurality of inputs, including measured signals, known metabolic inputs, reported uncertain metabolic inputs, raw estimated metabolic states, uncertain metabolic inputs, and reconciled uncertain metabolic inputs, all of which may be provided in time series.

Credibility based on the measured signals may evaluate continuity (e.g., the lack of continuity) or completeness of the time series data, and may include one or more of sensor assessed confidence threshold, calibration events, max gap size, floating scope, periodic scope, or the like.

Credibility based on the known metabolic inputs and raw estimated metabolic states and uncertain metabolic inputs may evaluate expected behaviors indicative of incomplete data or lack of unity, and may include one or more of expected correlations between inputs (uncertain or known), expected event counts, floating scope/periodic scope, and the like.

Credibility based on the reported uncertain metabolic inputs, raw estimated metabolic inputs, uncertain metabolic inputs and reconciled uncertain metabolic inputs may evaluate local variance vs. global variance (indicative of unannounced or unreported inputs), discrepancy between reported and estimated uncertain inputs, pattern matching, floating/periodic scope and the like.

The credibility assessor 310 aggregates the one or more credibility evaluations described above and provides (outputs) a credibility of final estimated metabolic state and reconciled estimate inputs, which may include the credibility as a time series.

The credibility assessor 310 may determine CGM continuity, quality of the fit, total carbs, number of carb events, carbs corresponding to BG artifacts, agreement with user-reported carbs, veracity of insulin data (especially in MDI (metered dose inhaler)), etc.

In some implementations, an aggregated sense of the credibility of data collected at a particular time of day may be obtained by averaging credibility scores at that time across multiple days. If the average value of credibility that time is low, then there may be a systematic issue with how the data is being collected. For example, if the patient is using a non-connected pen to bolus meals at work, then this would show up as a high value of insulin at that time of day, with high variability over time, which would translate into a low average credibility score at that time of day. As another example, if the patient is consistently acknowledging regular meals at times far away from estimated carbs, then this can lead to low credibility scores both at the time of actual eating and at the time of the acknowledgement of eating.

The input reconciler 330 reconciles uncertain untrusted user inputs with estimated inputs, wherein the reconciliation is based on one or more of measure signals, trusted metabolic inputs, untrusted metabolic inputs and model parameters. The methods do not necessarily evaluate a penalty of the estimate of the closeness to the reported, rather they may evaluate a sigmoidal wave of reported and estimated inputs over time. In some implementations, the methods may learn the patients' typical errors over time. The input reconciler 330 outputs reconciled estimates of metabolic inputs and disturbances for use in further processing and/or display.

The state estimator 340 provides an estimate of what was actually happening in the system. The process disturbances here are allowed to be nonzero (e.g., not zero mean) and not a measurement error. The output of the state estimator is an estimate of the states, which can be multiple vectors/matrix.

In one implementation, the state estimator receives the initial metabolic state (from past state estimates), the (vector of) known metabolic inputs, and the (vector of) reconciled uncertain metabolic inputs. Having estimated and reconciled the input time series, all that remains to compute is the associated state trajectory, which is output as a final estimated metabolic input vector.

In one exemplary model, the interaction of insulin to glucose clearance with two differential equations that include different types of insulin used for intensive insulin therapy (e.g., fast and long-acting) and different compartments of equilibration (e.g., liver) is captured. Other metabolic models could be used in this same framework for prospective and retrospective estimators. The tradeoff is between physiologic completeness and stability/observability. For example, simple models can combine details or compartments that are physiologically separate with several types of mass transport etc., whereas more complex models can resolve differences between patients or differences in glucose-insulin behavior over time. In practice, there are limits to the complexity of a model that can be observed using only CGM data and observational data (e.g., normal daily variation) because more complex models may require clinical studies with additional measurements like multiple tracers or well-described inputs such as OGTT (oral glucose tolerance test) or meals with known composition (fat/carbs/protein). However, the more complex model may be useful in solving the issue of inputs based on corruption.

Credibility determination may be performed here on the estimated metabolic state(s) independent of the credibility determination that may be performed on the reconciled untrusted metabolic inputs, including credibility of the reconciled estimated metabolic inputs and credibility of the estimated metabolic states.

The outputs of the retrospective input compiler 220R include reconciled estimated metabolic inputs which are the untrusted metabolic inputs that have been estimated and reconciled. The trusted metabolic inputs may be considered to be passthrough inputs and may thus be outputted in their original form in some implementations. It is noted that these inputs and outputs do not include uncertainty in the model parameters like insulin sensitivity.

Exemplary output of the retrospective input compiler 220R may include transients in the blood glucose signal that result from different effects (signature in BG variability) and a perturbation signal that describes the transients in the signal that vary from oral carbs and other affects, which may be divided as follows: OC (oral carb) mixed meal postprandial responses (adjusted to account for previous carbs and insulin delivery); signal explaining low-frequency variation in blood glucose concentration consistent with changes in insulin sensitivity; and signal explaining aspects of the blood glucose trace that cannot otherwise be interpreted as postprandial responses or changes in insulin sensitivity, such as variability due to changes in posture, physical activity, or (potentially) to meals that do not fit well the profile of a "mixed" meal.

An estimated net oral carb effect may also be determined. One meal may be split into several discrete carb signals. There can be glucose added from endogenous sources like the liver that are modelled as net oral carbs.

Other behavior or physiology that may be captured include, for example: glycemic consumption during exercise (acts like insulin as it increases glucose uptake); post-exercise changes in insulin sensitivity; daily variation of insulin sensitivity (diurnal variation); differences in insulin on board curves/insulin curves; and unlogged bolus.

The metabolic state estimates 345R comprise a time series of insulin and glucose levels in the compartments of the model and CGM signal.

A final reconciled meal history includes the time and net carbs. The delivered insulin is a passthrough of the retrospective input compiler 220R.

Thus, in the retrospective input compiler 220R, estimates of the metabolic state of the patient are constructed from the stream of the trusted data and now the stream of estimates of the untrusted data (associated with that estimated state trajectory for each period of time being estimated) has a credibility assessment (a confidence level that the patient ate something and when). This may be performed historically for last month's data, but also on the data newly received data, such as live data 212 described further herein e.g., with respect to live input compiler 220L.

Figure 4:
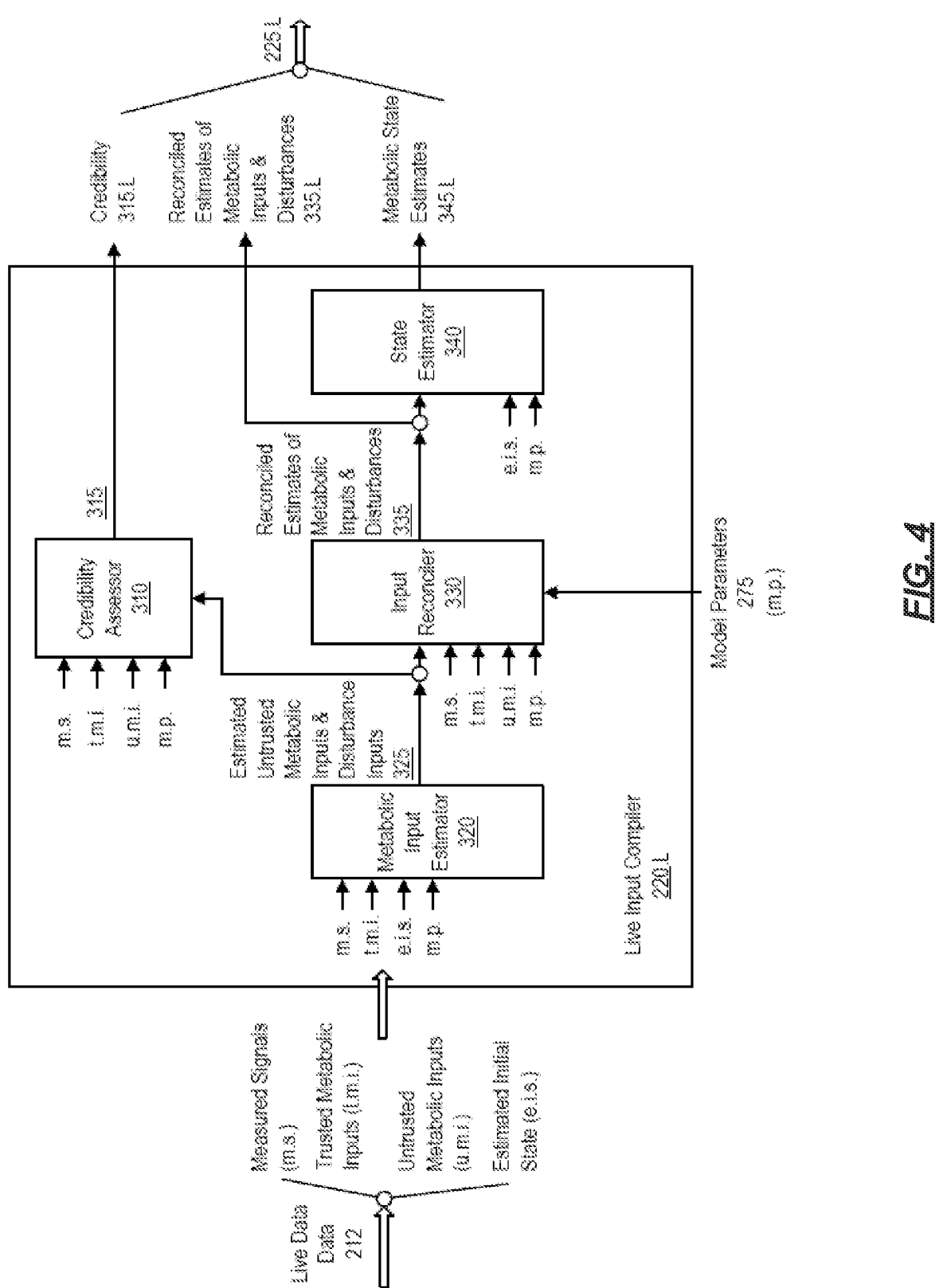
FIG. 4 is a block diagram an implementation of a live input compiler.

FIG. 4 is a block diagram of an implementation of a live input compiler 220L. The live input compiler 220L comprises the same components as the retrospective input compiler 220R, but uses live data 212 as the input instead of using retrospective data 210 as the input. Thus, like the retrospective input compiler 220R, the live input compiler 220L also comprises the metabolic input estimator 320, the credibility assessor 310, the input reconciler 330, and the state estimator 340.

The output fields of the live input compiler 220L are the same as those of the retrospective input compiler 220R, except that are based on the live data 212. As such, the outputs of the live input compiler include credibility 315L, recorded estimates of metabolic inputs and disturbances 335L, and metabolic state estimates 345L. In this manner, untrusted pieces of the live data 212 are reconciled based on other available data. For example, the metabolic inputs like carbs from the last 6 hours can be estimated, and the corresponding states for the last 6 hours and credibility for last 6 hours can also be estimated.

With the live input compiler 220L, a patient is interacting with the systems and methods in real time. Patients do not behave consistently like an AP system would and do not always provide accurate data (e.g., mis-reported carbs either from a counting issues, a timing issue, or both). One example application could suggest when and/or how much meal appeared to have been consumed, allowing the patient to confirm or deny, or modify the suggested meal information. This enables meal/exercise detection, as well as plasma glucose prediction. In the example of prediction of glucose, the systems and methods described herein are able to predict glucose for the next two hours using data from the last 6 hours. Additionally, credibility of the sensor data can be determined (how close to a calibration, is signal bumpy, is sensor out of range) and used in overall carb and insulin credibility measure. Similarly, insulin data credibility may be determined (missing basal data, unexplained drops in glucose concentration (unacknowledged bolus), etc.). The systems and methods allows for intelligent interaction and decision making knowing the reconciliation of the detected data with the reported data.

When dealing with live data, because of not having the benefit of the knowledge of future it is important to pay particular attention to the most recent value and its slope. E.g., require estimator to find agreement between the most recent points (last two) by weighting the most recent data more heavily. In one implementation, the input reconciler vector extracts the reported uncertain metabolic inputs for real time applications, wherein the resulting vector is such that the last entry corresponds to the current time. The extracted vector(s), in combination with vectors of raw estimated uncertain metabolic inputs, are combined in a function based on time-relevance and/or relative confidence as described below.

Example 1 (for live predictor): weighting is applied base on time-relevance, wherein recent reported inputs are most heavily weighted, long-time past reported inputs are lightly weighted and recent raw estimated inputs (if any) are lightly weighted. Because it requires future data.

Example 2 (applies to live or retrospective): weighting is applied based on relative confidence of the reported and estimated untrusted inputs, wherein the confidence is based on a user/system rating and/or a model-based confidence of the estimated inputs.

In one exemplary application, the systems and methods estimate carbohydrate intake independent of user input. With patients that treat diabetes using multiple daily injections (without a smart pen), data suggests this as the safest assumption. The systems and methods consider the situation when a patient reports a carbohydrate estimation that does not agree with the estimated carbohydrate independent of user input. Because the systems and methods cannot take both estimated and reported carbohydrate estimates to be true, the process of reconciliation is useful. Upon reconciliation, the systems and methods express of the result of reconciliation as a new pair of reconciled estimated inputs.

Figure 5:
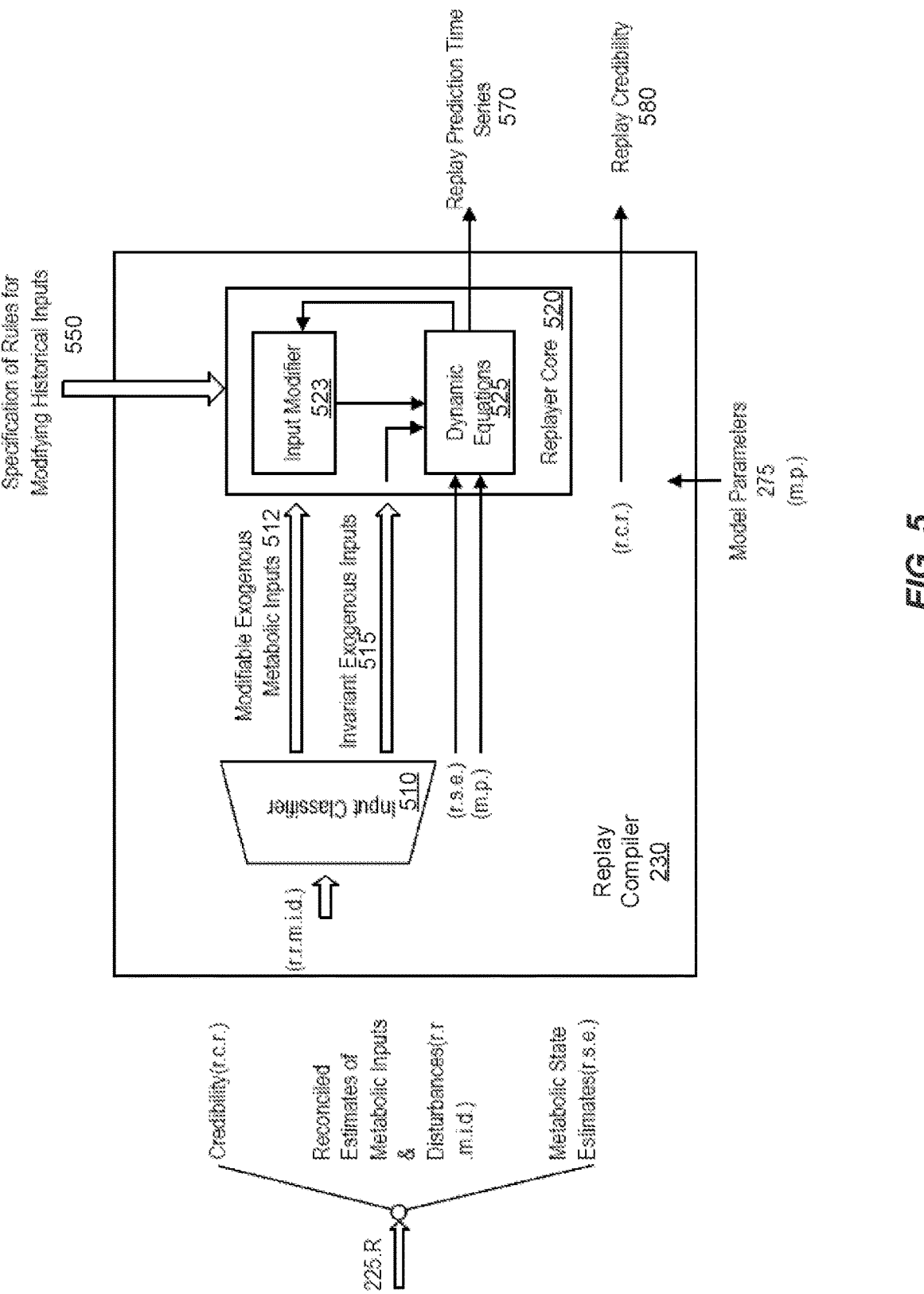
FIG. 5 is a block diagram an implementation of a replay compiler.

FIG. 5 is a block diagram an implementation of a replay compiler 230. The replay compiler 230 comprises an input classifier 510 and a replayer core 520. The replayer core 520 comprises an input modifier 523 and dynamic equations 525. The replay compiler 230 performs a replay of glucose traces by modifying inputs to determine an impact of the modified input. The replay compiler 230 provides a machine for assessing BG, insulin, meal, and behavioral outcomes at different scopes (individual/population) with different masks (closed-loop, sleep, credible, etc.). The systems and methods take any non-optimal intervention in diabetes, simulates scenarios to determine an optimal intervention and quantifies effect of optimal intervention—either as a CGM trace or glycemic effect of optimal vs. non-optimal.

The inputs to the replay compiler 230 are the retrospective compiled inputs (i.e., the output 225R of the retrospective input compiler 220R) including credibility 315R, reconciled estimates of metabolic inputs and disturbances 335R, and metabolic state estimates 345R (e.g., estimated metabolic states, final reconciled estimated metabolic inputs, known metabolic inputs and alternative metabolic inputs (specific inputs or strategies for the duration of the time series)). In some implementations, the inputs include all of the metabolic inputs (trusted and reconciled estimates of untrusted) as a time series and credibility.

The input classifier 510 receives the reconciled estimates of metabolic inputs and disturbances as input and classifies each data as a modifiable exogenous metabolic input 512 or an invariant exogenous input 515.

In some implementations, a trusted piece of data (e.g., insulin) may be modified. In other implementations, a trusted piece of data and an untrusted piece of data (e.g., meal data) may be modified. In other implementations, all the inputs may be modified.

A variety of scenarios may be contemplated with the replay compiler 230: A) all untrusted reconciled data is modified in the replay function; B) some but not all untrusted reconciled data is modified in the replay function; C) some trusted data is modified in the replay function; and D) combinations of B) and C). In general, the replay compiler 230 modifies at least some data and runs at least one simulation. For example, it may be a trusted piece of data, like insulin. Sometimes, it is both a trusted piece of data and an untrusted piece of data, like both insulin and meals (e.g., replacing the reconciled bolusable carbs with some other scripted meal behavior, leaving the signature of BG variability as the only thing that is not modified). In an exemplary embodiment, all inputs are modified.

The replayer core 520 comprises the input modifier 523 and dynamic equations 525. The input modifier 523 receives the modifiable exogenous metabolic inputs 512 and a specification of rules for modifying historical inputs 550 (referred to also as a specification of rules 550).

The inputs 512 are thus modified at the input modifier 523 using the specification of rules 523. The specification of rules 523 are "what if" scenarios that are to be tested to determine an outcome based on a modification of an input. Rules may be selected by the user individually and/or based on preset scenarios. Some rules that may be specified compare the following: Conversion of MDI to CSII (continuous subcutaneous insulin infusion) or vice versa, long-acting dosage/timing, basal rate profiles, recognition/removal of hypoglycemia treatments in the historical data, revising of historical boluses, revising of bolus does parameters, insertion of prospective hypoglycemia treatments at times where alternative insulin input create new instances of hypoglycemia, replacement of instances of historical meals with a prospective model, replacement of historical acknowledgements of carbs with a prospective acknowledgement model (e.g., acknowledging carbs at times close to estimated carbs).

Additional specification of rules may be designed to process and evaluate: exercise and/or how to optimize treatment around exercise; treatments to include rescue carbs (e.g., amount required); treatments to include other meal bolusing strategies (e.g., split, delayed, and extended boluses); and type 2 treatments including oral medications, etc.

Specification of rules may be provided directly by the patient, based on a call of a particular pre-programmed function, based on a user interface, such as reporting and analysis software and/or other interfaces that allow the user to select a particular scenario ("what if I bolused earlier"), ask a specific questions ("what if I were on pump therapy")

and/or modify specific inputs ("what if I take two additional units of insulin when I bolus"), or the like, as may be appreciated by one skilled in the art. The selections may be real time or retrospective and may be presented at a variety of levels of granularity.

The output of the input modifier 523 are provided to the dynamic equations 525 as input along with the invariant exogenous inputs 515, the metabolic state estimates, and the model parameters 275.

In an implementation, the dynamic equations may use an individual mathematical model that is a compartmental model of the metabolic processes that produce or consume glucose in the body. For example, this model has terms that describe the increase in glucose following meals and the uptake of this glucose into muscles and adipose tissue that is stimulated by insulin. The model is individualized to account for between-subject differences in the insulin action and meal metabolism and diabetes.

The dynamic equations 525 perform replay on the inputs. Replay runs model-based estimation using any known model-based approach that takes into account meal and/or insulin parameters. For example, the model may use standard mixed meal that is a typical combination of carbs, protein and fat. However, other meal signatures may be used, e.g., high carb/glycemic meal and/or low carb/glycemic meal, or even a combination of various types of meals. Some implementations may add long-acting meals versus short-acting meals based on composition and glycemic index, etc. This would run as part of the reconciliation. If the meal action is significantly different from the standard meal, then it may be explained in a way that is less physiologic accurate. For example, 30 g of carbs from pizza would be estimated by a 30 g initial meal followed by two 10 g meals.

In an implementation, the estimation of metabolic states are performed for the duration of the input time series and play forward the individualized mathematical model to the end of the input time series.

The model parameters 275 are an optional estimate useful, but not essential, as a feedback input to make the parameters more individualized for the patient.

Replay credibility 580 is determined by the replay compiler and output. The replay compiler 230 identifies and outputs credible instances of particular scenarios (samples) in the replay analysis. This may be performed by scoring each sample (e.g., each replay analysis result) with a credibility score. For example, identifying credible instances of successfully avoiding hypoglycemia; failing to avoid hypoglycemia, and/or skipped or significantly delayed meal boluses. The average credibility score of samples in a data set in replay analysis gives an overall sense of the significance/believability of the replay result, which may be useful in interpreting the results.

A comparator may be comprised within the replay compiler 230 to compare the various time series from the dynamic equations 525 based on the credibility of the data (weighted so that less credible data is ignored or has low weighting). Another example if the signatures of BG variability are to erratic, data may become non-credible during that time period. One skilled in the art appreciates that there are many ways to recognize the patient data is inconsistent with the model.

In an implementation, BG outcome metrics are assessed in replayed time series based one more or more of: sample means, sample variance, time-in-range, episodes of high/low BG, low blood glucose risk, high blood glucose risk, overall risk. Unlike a conventional technique that computes average blood glucose by equally weighing all samples, here the credibility score of each sample is used to determine the weight that each sample has in the average.

The output of the dynamic equations 525 comprises replay prediction time series 570. The output (the time series 570) may be provided to the input modifier 523 for subsequent use and may include replay simulated metabolic states resulting from alternative inputs with credibility scores. The output may include the simulated time series, the result of the compared time series (worst/best/actual), a recommendation based on the compared time series, and any other data processed by the system (e.g., credibility score).

In some embodiments, the replay compiler 230 functional output could be a reproduced (simulated) CGM trace that the patient actually experienced. The replay compiler 230 is a function that when run on historical CGM reproduces the trace, in which case the CGM trace would be a smoothed version of the CGM trace without the sensor imprecision, and including additional information for example can reproduce additional correlative data (e.g., meals) not provided by patient.

In therapy optimization in DSS (decision support system) or AP use cases, the replay compiler 230 could optimize therapies, such as total daily basal, wherein the input would be parameter to be optimized (actual basal insulin), output would be optimized version of that input (optimal basal insulin). Replay simulates optimal prescription amount/time of parameter (total daily basal in one example).

In patient education use cases, a dynamic report (retrospective or real time) may be generated that allows a patient to highlight or drag through scenarios and see the results of the "what if scenarios" returned from the replay compiler 230. For example, a slider bar in a graphical user interface may allow a patient (or other user) to slide things around and then see the impact resulting from the replay analysis (more carbs, less carbs, higher glycemic, lower glycemic, earlier bolus, later bolus, more insulin, less insulin, etc.).

In some embodiments, providing an output of the average credibility score of samples in a data set in replay analysis gives an overall sense of the significance/believability of the replay result.

In some embodiments, a risk stratification tool for health care professionals may be provided as output that identifies patients by a particular category or need, e.g., patients with least premeal bolusing compliance, and may include the potential benefits of therapy adjustments.

In some embodiments, output may highlight/prioritize the most impactful potential changes in a reporting interface (e.g., changing insulin timing versus bolus amounts or highlight best meals).

In some embodiments, output may trigger coaching comments and discussion points via coaching call or chatbot prompts.

Figure 6:
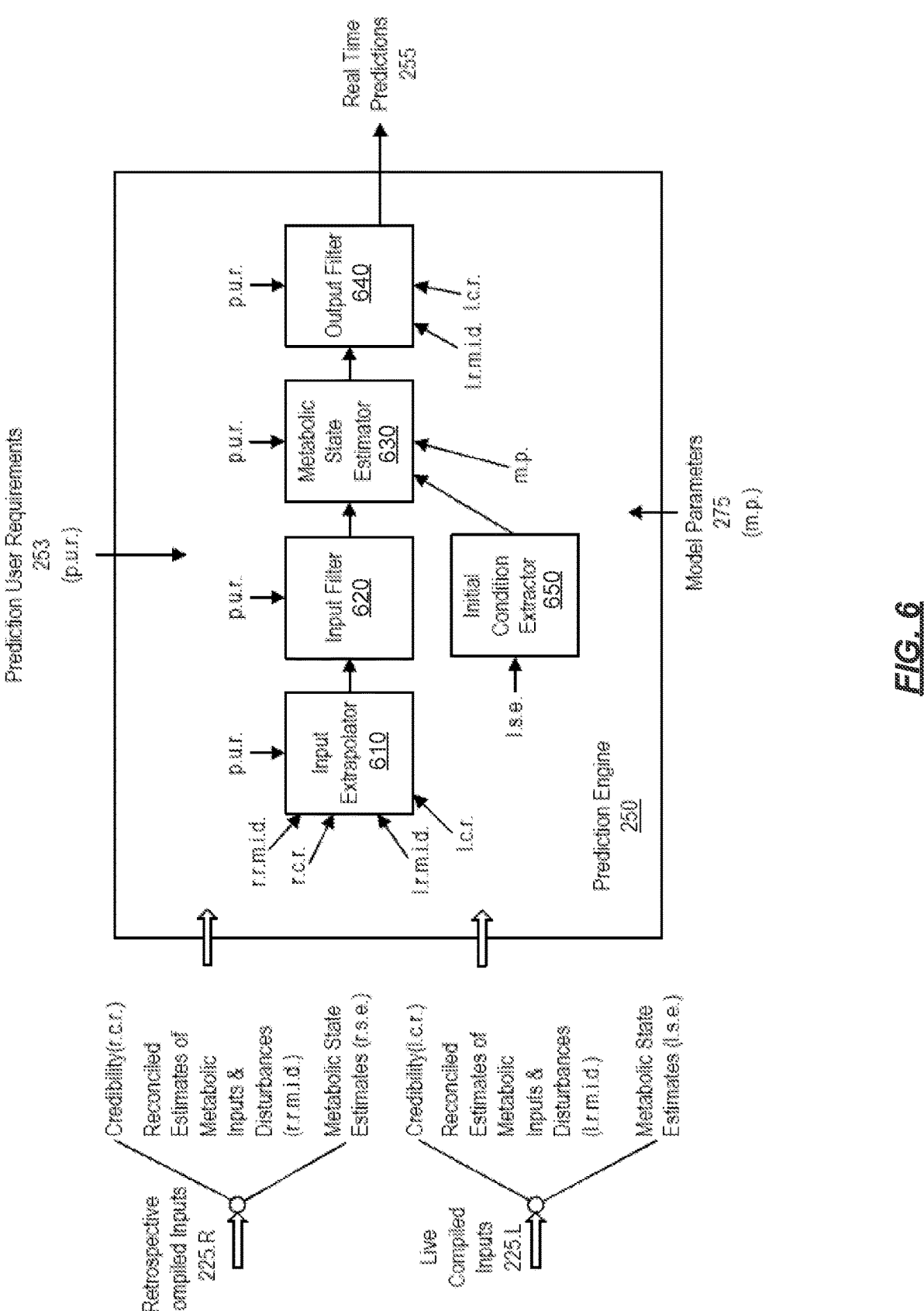
FIG. 6 is a block diagram of an implementation of a prediction engine.

FIG. 6 is a block diagram of an implementation of a prediction engine 250. The prediction engine 250 receives the retrospective compiled inputs 225R and the live compiled inputs 225L as inputs, along with the model parameters 275 and the prediction user requirements 253, and outputs real time predictions 255.

The initial state of the prediction engine 250 would describe the amount of insulin and carbohydrates that are already in the body and acting on the glucose level. With no additional action, the prediction engine 250 would predict future metabolic states such as a glucose excursion from a previous meal as well as hypoglycemic events. Prediction is extrapolation of reconciliation from the input compiler 220. In other words, prediction is also responsive to historic data as well as reconciled data.

The prediction engine 250 comprises an input extrapolator 610, an input filter 620, a metabolic state estimator 630, an output filter 640, and an initial condition extractor 650.

The input extrapolator 610 uses the prediction user requirements 253, the credibility and the reconciled estimates of metabolic inputs and disturbances from the retrospective compiled inputs 225R, and the credibility and the reconciled estimates of metabolic inputs and disturbances from the live compiled inputs 225L to perform extrapolation. The extrapolated data is provided from the input extrapolator 610 to the input filter 620.

The input extrapolator 610 extrapolates the input time series to account for (1) additional information about the future available in real time (e.g., expected meals, exercise, etc.) and (2) signatures of BG variability.

The input extrapolator 610 may use the retrospective compiled inputs 225R to make inferences based on historical data, e.g., use recent past of signatures of BG variability (i.e., disturbances) and effect of historical signatures of BG variability. Signatures of BG variability may be used to interpret data as it goes farther into the prediction horizon.

The prediction engine 250 may project disturbances (signature of BG variability) which shows the trend of inaccuracies in the data resulting from differences in reconciled data. A disturbance signal is a result of the reconciliation process, and may be considered to be an estimated unknown signal. For example, a disturbance could result from circadian rhythms, exercise trends, etc. The accuracy of prediction depends on different assumptions about the future based on the nature of the disturbance.

The input filter 620 filters the extrapolated data with the prediction user requirements 253 and provides its output to the metabolic state estimator 630.

Depending on the implementation, the input filter 620 is optional, however it may be useful when other filtering or smoothing has not been applied to one or more of the inputs. The input filter 620 filters or smooths the extrapolated input time series to prevent jitter in predicted trajectories to (1) sensor noise and (2) rapidly evolving understanding of recent untrusted inputs. In some implementations, the input filter 620 uses a low pass filter to minimize jitter in the predicted trajectories in successive updates.

The initial condition extractor 650 extracts data from the metabolic state estimates of the live compiled inputs 225L and provides the extracted data to the metabolic state estimator 630.

The metabolic state estimator 630 receives the filtered data and the extracted data as inputs along with the prediction user requirements 253 and the model parameters 275. The metabolic state estimator 630 processes these inputs and provides output to the output filter 640.

The metabolic state estimator 630 receives the (optionally filtered) extrapolated inputs(s), the extracted initial condition and the model parameters to the extent an individualized physiological model is being used by the estimator. A variety of estimators may be useful. In one embodiment, the metabolic state estimator 630 performs an open-loop estimate of metabolic states into the future from the best estimates of the metabolic state vector at the beginning of the time series, playing forward the individualized physiological model all the way to the end of the prediction horizon.

In some implementations, the metabolic state estimator 630 may use an individual mathematical model, which is a compartmental model of metabolic processes that produce or consume glucose. For example, this model has terms that describe the increase in glucose following meals and the uptake of this glucose into muscles and adipose tissue that is stimulated by insulin.

The output filter 640 filters the output from the metabolic state estimator 630 along with the prediction user requirements 253 and the credibility and the reconciled estimates of metabolic inputs and disturbances from the live compiled inputs 225L and provides its output as the real time predictions 255. The output filter 640 can be used to constrain the real time predictions 255 depending on the live compiled inputs 225R.

The output filter 640 is an output module that renders a predicted output time series (i.e., the real time predictions) to (1) allow dramatic changes in predicted trajectories only when there are recognizable and significant changes in reconciled inputs and/or (2) filter/smooths or otherwise prevent jitter in the predicted trajectories due to sensor noise.

The real time predictions 255 (i.e., live predictions) may be a predictive profile of future BG (e.g., in vector form) and can be used to inform decision making going forward. For example, a prediction might show upcoming hypoglycemia, and the prediction may then be used to alert and/or cause a patient to ingest fast acting glucose tablets. Reconciliation and prediction as described herein allow for more responsiveness to patient behavior change and therefore better prediction of metabolic state.

In some implementations, the real time predictions 255 are a vector of predicted metabolic state. The stability of the resulting prediction remains stable until there are markers of an impending state changes (e.g., meals and insulin allow a more dynamic output). Patient provided input and detected input leads to credible changes when the patient is expecting it.

In some implementations, the prediction engine 250 may apply conditional weighting to data, wherein the historical data may be weighted according to (1) time of day, (2) features of the current estimated state, and (3) side information. The conditional weighting is based on final estimated metabolic states, a database of past metabolic inputs (trusted and untrusted) and side information in some implementations.

Signature of BG variability into the future is a key differentiator in the prediction engine 250. Additional key advantages, which may be used alone or in combination, include: reconciled meals; input extrapolation (e.g., meals set to zero); and signature of BG variability informed by time day from retrospective models and daily trend. Typically, for predictor in real time this is rerun for the last 6 hours of data starting point.

Weighting of the signature of BG variability is dependent on the deference to the patient and depending on available reported vs. reconciled data and the credibility thereof (e.g., depends on time since event).

The systems and methods described herein have a tradeoff of the time domain predictions, wherein more weight is given to the reconciled inputs to the most immediate value. The conditional weighting allows these models to be tuned to specific variations.

In some implementations, credibility is calculated for the predicted state based on the credibility of the inputs, including raw inputs and reconciled inputs. Uses of credibility in real time prediction with reconciliation include: (1) confidence of medical actions determined via reconciled projection, namely, if the prevailing credibility score is low (e.g., due to low confidence in recent CGM samples, or to evidence of unacknowledged meals and/or boluses), then corresponding resulting reconciled projection may be not credible, and (2) determination of the need to wait before offering advice based on reconciled projection, namely, if the prevailing credibility score is low, then the patient may be advised to wait a while longer before a recommendation is rendered.

Figure 7:
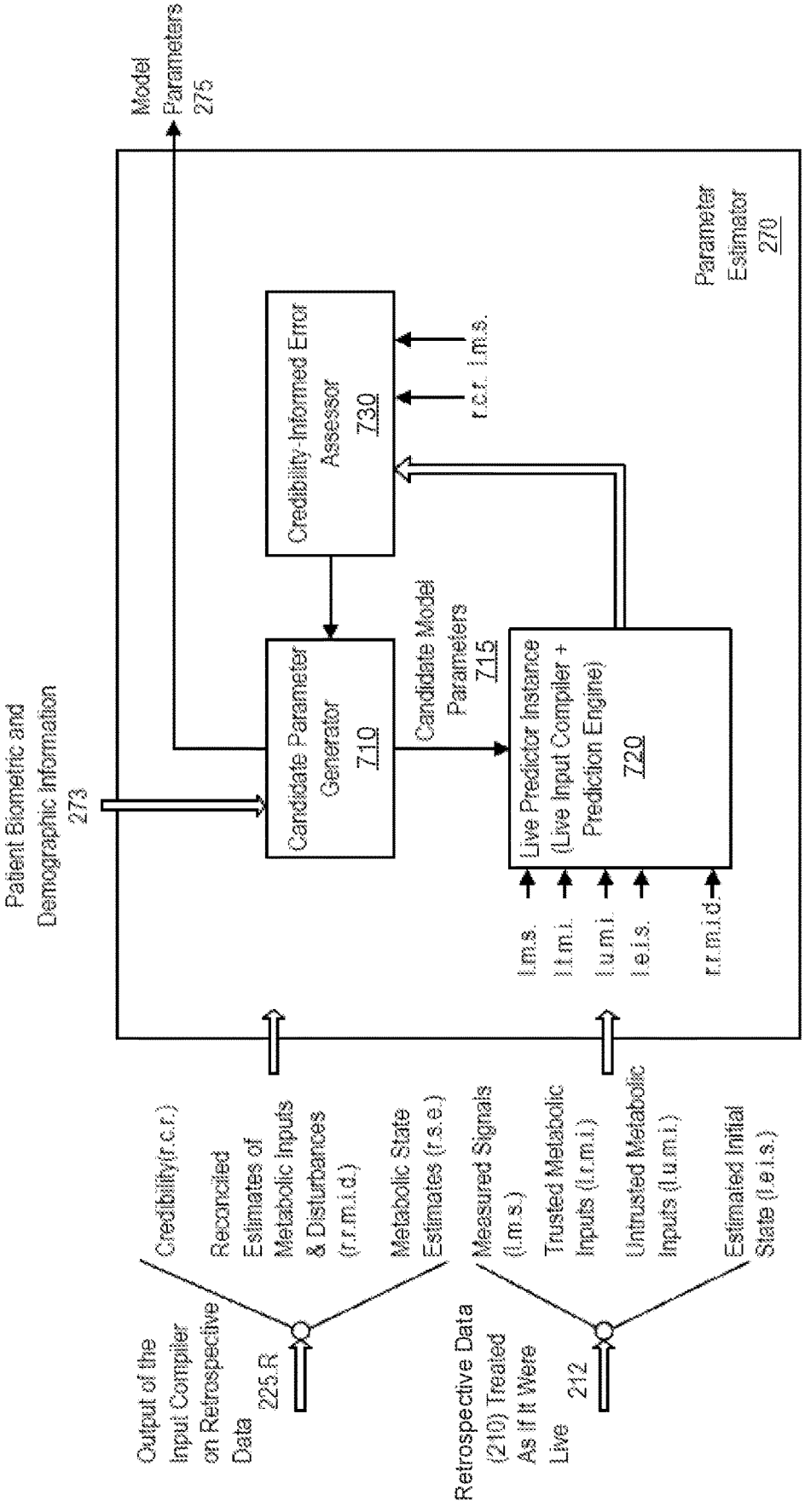
FIG. 7 is a block diagram of an implementation of a parameter estimator.

FIG. 7 is a block diagram of an implementation of a parameter estimator 270. The parameter estimator 270 is configured to perform parameter optimization. The parameters are tuned only on reconciled, credible data. Parameter optimization is applied to get the best settings for metabolic model parameters based on a retrospective data set. Over time the predictor can be run retrospectively to improve prediction. The model is optimized to give the best predictive model performance. Parameter estimation is optional and depends on the type of estimation used in the previous blocks and what type of model is used for that estimation.

The parameter estimator 270 is built to make the optional individualized physiological model used by the prediction engine as accurate as possible by optimizing the estimated model parameters 275 that are provided as output. The goal is to estimate physiological parameters of the patients, generic application, e.g., insulin sensitivity, absorb lipro (medication) absorption rate, any physiological, etc.

In practice, the optimization uses retrospective data, runs the predictor on that data, builds the prediction engine, apples to retrospective data as if it was live and looks to see how accurately it produces predictions of the retrospective trace, tuning of the parameter is based on accuracy of simulated predictions The parameter estimator 270 receives the retrospective compiled inputs 225R and the retrospective data 210 data as inputs, along with patient biometric and demographic information 273, and outputs model parameters 275.

The parameter estimator 270 comprises a candidate parameter generator 710, a live predictor instance 720 (which comprises a live input compiler and prediction engine), and a credibility-informed error assessor 730.

The candidate parameter generator 710 generates candidate model parameters 715.

The live predictor instance 720 uses the candidate model parameters 715, the retrospective data 210 (treating the retrospective data 210 as if it were live data), and the reconciled estimates of metabolic inputs and disturbances of the retrospective data 225R, and provides its output to the credibility-informed error assessor 730.

The credibility-informed error assessor 730 receives the output of the live predictor instance 720 and uses this data along with the credibility of the retrospective data 225R and the measured signals of the retrospective data 210 to generate output that is provided to the candidate parameter generator 710 for subsequent use in determining the model parameters 275.

In an implementation, the reference glucose concentration and the insulin sensitivity for each subject is tuned to the optimized value of a list of possible values. The predictor may run over 30 days of data (e.g., insulin, CGM and meal, etc.) and determine the best predictor for 1 hour out.

FIG. 8 is an operational flow of an implementation of a method 800 for reconciling data. The method 800 may be performed by the platform 200 for example. Aspects of the method 800 may be performed by the input compiler 220 in some implementations.

At 810, untrusted data pertaining to a subject is received at an input estimator, such as the metabolic input estimator 320 of the retrospective input compiler 220R or the metabolic input estimator 320 of the live input compiler 220L. The untrusted data may be comprised within retrospective data, such as the retrospective data 210, or live data, such as the live data 212. The untrusted data comprises at least one of timing of insulin, amount of insulin, meal data, or activity data, wherein the untrusted data is untrusted because of behavioral anomalies or human error in at least one of timing, amount, estimation, or entry.

At 820, trusted data pertaining to the subject is received at the input estimator. The trusted data may be comprised within retrospective data, such as the retrospective data 210, or live data, such as the live data 212. The trusted data comprises at least one of CGM data, insulin pump data, computer generated data, computer generated models, or an individualized model that describes the glucose and insulin dynamics of the subject.

At 830, the untrusted data is reconciled using the trusted data. The input reconciler may perform the reconciliation of the untrusted data using the trusted data. In particular, (1) after the input estimator uses the trusted inputs, along with the mathematical model, to estimate values for the untrusted inputs, (2) the untrusted input data are fused with the estimated untrusted inputs to produce a final reconciled untrusted data set. The untrusted inputs and estimated untrusted inputs can be fused in different ways depending on the application context and temporal scope. In some cases, such as when the estimated untrusted inputs are estimated with low error covariance, or when the estimated inputs have proven to accurately predict the blood glucose over time, or when the untrusted data source has proven to be completely untrustworthy, the reconciled untrusted data can be derived exclusively from the estimated inputs independent of the untrusted data. In other cases, when the mathematical model and/or the estimated inputs fail to be predictive of blood glucose over time, or when the untrusted source of data is able to demonstrate accuracy by independent means, the reconciled untrusted data can be derived exclusively from the untrusted inputs themselves. In live application contexts (non-retrospective applications), or when additional data are required to make a determination of whether the current estimated untrusted inputs are more reliable than the untrusted inputs themselves, then the reconciled untrusted data can be computed as a blend of the untrusted inputs and the estimated untrusted inputs, where (1) for the recent past the reconciled result defers to the untrusted data (because more data is needed to refute it), (2) for the distant past the reconciled result defers to estimated untrusted inputs, and (3) in the transition region between recent and distant past, the reconciled value is computed as a weighted average of the untrusted input data and the estimated untrusted input data depending on the proximity to the current time. Alternatives to the weighted average include (1) probabilistically selecting either the untrusted input or the estimated untrusted input based on the perceived reliability of the of the untrusted or estimated untrusted data or (2) choosing the untrusted input or estimated untrusted input to maximize a classification objective, e.g., maximum likelihood or maximum a posteriori probability.

At 840, the reconciled untrusted data is outputted, e.g., from the input compiler 220.

FIG. 9 is an operational flow of another implementation of a method 900 for reconciling data. The method 900 may be performed by the platform 200 for example. Aspects of the method 900 may be performed by the input compiler 220 in some implementations.

At 910, untrusted data pertaining to a subject is received, at an input estimator, such as the metabolic input estimator 320 of the retrospective input compiler 220R or the metabolic input estimator 320 of the live input compiler 220L.

The untrusted data may be comprised within retrospective data, such as the retrospective data 210, or live data, such as the live data 212. The untrusted data comprises user entered data comprising at least one of insulin data, meal data, or activity data.

At 920, the untrusted data is reconciled using trusted data pertaining to the subject. The trusted data may be comprised within retrospective data, such as the retrospective data 210, or live data, such as the live data 212. The trusted data comprises computer generated data. The reconciliation may be performed using an input reconciler. In particular, (1) after the input estimator uses the trusted inputs, along with the mathematical model, to estimate values for the untrusted inputs, (2) the untrusted input data are fused with the estimated untrusted inputs to produce a final reconciled untrusted data set. The untrusted inputs and estimated untrusted inputs can be fused in different ways depending on the application context and temporal scope. In some cases, such as when the estimated untrusted inputs are estimated with low error covariance, or when the estimated inputs have proven to accurately predict the blood glucose over time, or when the untrusted data source has proven to be completely untrustworthy, the reconciled untrusted data can be derived exclusively from the estimated inputs independent of the untrusted data. In other cases, when the mathematical model and/or the estimated inputs fail to be predictive of blood glucose over time, or when the untrusted source of data is able to demonstrate accuracy by independent means, the reconciled untrusted data can be derived exclusively from the untrusted inputs themselves. In live application contexts (non-retrospective applications), or when additional data are required to make a determination of whether the current estimated untrusted inputs are more reliable than the untrusted inputs themselves, then the reconciled untrusted data can be computed as a blend of the untrusted inputs and the estimated untrusted inputs, where (1) for the recent past the reconciled result defers to the untrusted data (because more data is needed to refute it), (2) for the distant past the reconciled result defers to estimated untrusted inputs, and (3) in the transition region between recent and distant past, the reconciled value is computed as a weighted average of the untrusted input data and the estimated untrusted input data depending on the proximity to the current time. Alternatives to the weighted average include (1) probabilistically selecting either the untrusted input or the estimated untrusted input based on the perceived reliability of the of the untrusted or estimated untrusted data or (2) choosing the untrusted input or estimated untrusted input to maximize a classification objective, e.g., maximum likelihood or maximum a posteriori probability.

Figure 10:
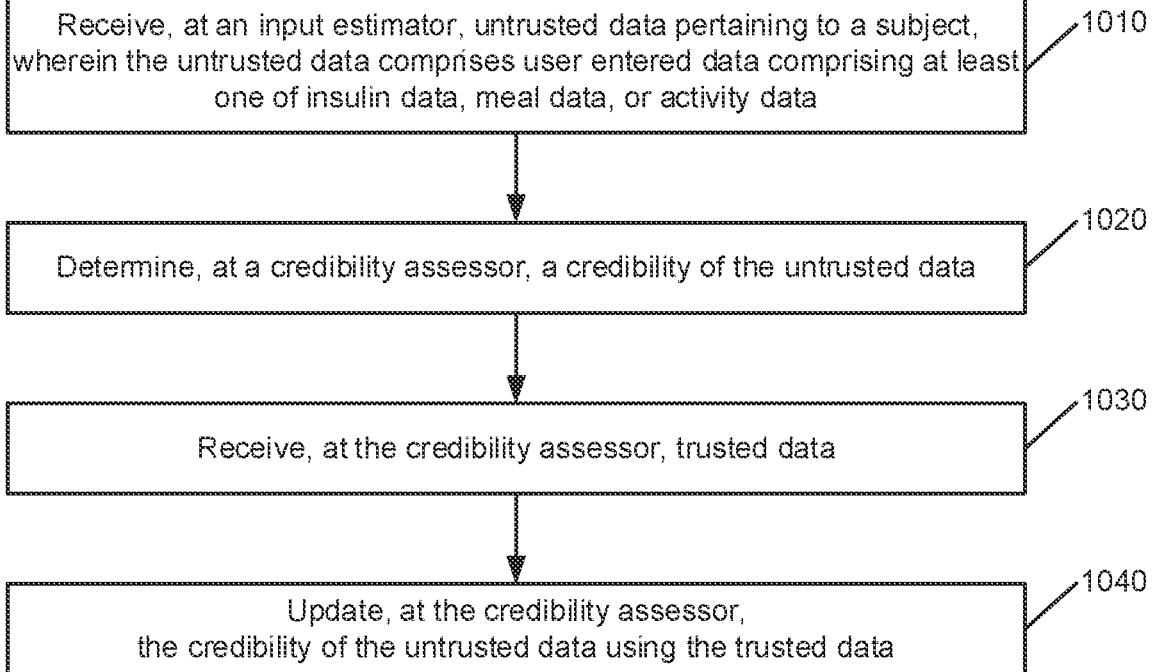
FIG. 10 is an operational flow of an implementation of a method for determining the credibility of data.

FIG. 10 is an operational flow of an implementation of a method 1000 for determining the credibility of data. The method 1000 may be performed by the platform 200 for example. Aspects of the method 1000 may be performed by the input compiler 220 in some implementations.

At 1010, untrusted data pertaining to a subject is received, e.g., at an input estimator, such as the metabolic input estimator 320 of the retrospective input compiler 220R or the metabolic input estimator 320 of the live input compiler 220L. The untrusted data may be comprised within retrospective data, such as the retrospective data 210, or live data, such as the live data 212. The untrusted data comprises user entered data comprising at least one of insulin data, meal data, or activity data.

At 1020, a credibility of the untrusted data is determined. The credibility may be determined by a credibility assessor, such as the credibility assessor 310 of the retrospective input compiler 220R or the credibility assessor 310 of the live input compiler 220L. Credibility of the untrusted data is assessed from characteristics of the untrusted data alone at one or more time scales. In particular, failure to acknowledge meals and/or insulin and/or physical activity over a period of time can be interpreted as incomplete data rendering the whole time period as not credible, e.g., with a credibility value of zero. Similarly, other data artifacts, such as double entries or unusually large (or small) insulin doses and/or acknowledged amounts of carbs or physical activity over a period time can be interpreted as non-physiological or behaviorally unlikely, again rendering the time period as not credible. Similarly, transient inaccuracy of generally trusted inputs can cause them to be treated temporarily as untrusted inputs, e.g., temporary non availability of sensor readings or temporary out-of-range indications from the sensor, again causing the associated periods of time as not credible.

At 1030, trusted data is received at the credibility assessor. The trusted data may be comprised within retrospective data, such as the retrospective data 210, or live data, such as the live data 212.

At 1040, the credibility of the untrusted data is updated using the trusted data. The updating may be performed by the credibility assessor. Credibility of the untrusted data can be assessed based on the extent to which it agrees with the estimated untrusted input data at one or more time scales. Specifically, when the underlying model has proven to be predictive of blood glucose concentration over time and when the untrusted inputs for a period of time differ from the estimated untrusted inputs, then the untrusted data can be assigned a low level of credibility for that period of time, e.g., closer to zero than one. Independently, a credibility value can be assigned to the reconciled untrusted inputs based on how the reconciliation is achieved. For example, if the model has proven to be highly predictive of blood glucose over time, the estimated untrusted inputs are highly consistent with the trusted data, and when the reconciled untrusted data is computed to be equal or very close to the estimated untrusted data, then the reconciled untrusted data can be assigned a high value of credibility, e.g., close to one, even when the corresponded untrusted data is not credible.

FIG. 11 is an operational flow of another implementation of a method 1100 for determining the credibility of data. The method 1100 may be performed by the platform 200 for example. Aspects of the method 1100 may be performed by the input compiler 220 in some implementations.

At 1110, first untrusted data pertaining to a subject is received, e.g., at an input estimator, such as the metabolic input estimator 320 of the retrospective input compiler 220R or the metabolic input estimator 320 of the live input compiler 220L. The first untrusted data may be comprised within retrospective data, such as the retrospective data 210, or live data, such as the live data 212. The untrusted data comprises user entered data comprising at least one of insulin data, meal data, or activity data.

At 1120, a credibility of the first untrusted data is determined at the credibility assessor, such as the credibility assessor 310 of the retrospective input compiler 220R or the credibility assessor 310 of the live input compiler 220L. Credibility of the untrusted data is assessed from characteristics of the untrusted data alone at one or more time scales. In particular, failure to acknowledge meals and/or insulin and/or physical activity over a period of time can be interpreted as incomplete data rendering the whole time period as not credible, e.g., with a credibility value of zero. Similarly, other data artifacts, such as double entries or unusually large (or small) insulin doses and/or acknowledged amounts of carbs or physical activity over a period time can be interpreted as non-physiological or behaviorally unlikely, again rendering the time period as not credible. Similarly, transient inaccuracy of generally trusted inputs can cause them to be treated temporarily as untrusted inputs, e.g., temporary non availability of sensor readings or temporary out-of-range indications from the sensor, again causing the associated periods of time as not credible.

At 1130, second untrusted data pertaining to the subject is received, e.g., at the input estimator, such as the metabolic input estimator 320 of the retrospective input compiler 220R or the metabolic input estimator 320 of the live input compiler 220L. The second untrusted data may be comprised within retrospective data, such as the retrospective data 210, or live data, such as the live data 212.

At 1140, a credibility of the second untrusted data is determined at the credibility assessor, such as the credibility assessor 310 of the retrospective input compiler 220R or the credibility assessor 310 of the live input compiler 220L.

At 1150, the credibility of the first untrusted data is updated using the second untrusted data and/or the credibility of the second untrusted data, depending on the implementation. The updating may be performed at the credibility assessor 310.

At 1160, trusted data is received at the credibility assessor 310. The trusted data may be comprised within retrospective data, such as the retrospective data 210, or live data, such as the live data 212.

At 1170, the credibility of the first untrusted data and the second untrusted data is updated using the trusted data. The updating may be performed by the credibility assessor. Credibility of the untrusted data can be assessed based on the extent to which it agrees with the estimated untrusted input data at one or more time scales. Specifically, when the underlying model has proven to be predictive of blood glucose concentration over time and when the untrusted inputs for a period of time differ from the estimated untrusted inputs, then the untrusted data can be assigned a low level of credibility for that period of time, e.g., closer to zero than one. Independently, a credibility value can be assigned to the reconciled untrusted inputs based on how the reconciliation is achieved. For example, if the model has proven to be highly predictive of blood glucose over time, the estimated untrusted inputs are highly consistent with the trusted data, and when the reconciled untrusted data is computed to be equal or very close to the estimated untrusted data, then the reconciled untrusted data can be assigned a high value of credibility, e.g., close to one, even when the corresponded untrusted data is not credible.

FIG. 12 is an operational flow of an implementation of a method 1200 for using untrusted data to provide output based on glycemic effects. The method 1200 may be performed by the platform 200 for example.

At 1210, data over a time period is predicted for a subject, e.g., by the prediction engine 250. In some implementations, (1) the initial condition (corresponding the state of the system in the past), the trusted inputs from that time in the past, and the reconciled untrusted inputs from that time in the past are used as inputs to the underlying mathematical model producing an estimate of the patient's current metabolic state and (2) accounting for expected future inputs (e.g., assumed insulin dosing, physical activity, and/or eating behavior), the mathematical model is used to predict future metabolic states of the patient including future blood glucose. Further features and details are described herein with respect to FIG. 6, for example.

At 1220, untrusted data directed to management of diabetes is received e.g., at an input estimator, such as the metabolic input estimator 320 of the retrospective input compiler 220R or the metabolic input estimator 320 of the live input compiler 220L. The untrusted data may be comprised within retrospective data, such as the retrospective data 210, or live data, such as the live data 212.

At 1230, a plurality of predictive data traces are simulated over the time period, e.g., by the replay compiler 230. A spectrum of possible variances of the untrusted data is used.

At 1240, the simulated predictive data traces are compared to the predicted data to identify glycemic effects, by the replay compiler 230.

At 1250, a visualization and/or a recommendation based on the glycemic effects are generated and outputted, by the replay compiler.

FIG. 13 is an operational flow of an implementation of a method 1300 for using replay prediction. The method 1300 may be performed by the platform 200 for example. Aspects of the method 1300 may be performed by the replay compiler 230 in some implementations.

At 1310, estimated metabolic states, reconciled estimated metabolic inputs, known metabolic inputs, and alternative metabolic inputs are received at the replay compiler 230.

At 1320, at the replay compiler 230, replay prediction is performed using the estimated metabolic states, the reconciled estimated metabolic inputs, the known metabolic inputs, and the alternative metabolic inputs. In some implementations, after specifying which historical inputs are modifiable (those that are either wholly new or are evaluated dynamically as a function of the newly predicted metabolic state of the patient) and which inputs are invariant exogenous inputs, the underlying mathematical model (as represented by the dynamic equations) is used to iteratively predict what metabolic states would have been experienced by the patient due to the modified inputs over some part of (or all of) the time period described by the retrospective data. The credibility of the retrospectively predicted estimates of the patient's metabolic state is determined from the credibility of the corresponding untrusted retrospective data. Further features and details are described herein with respect to FIG. 5, for example.

At 1330, replay simulated metabolic states based on the replay prediction are outputted by the replay compiler 230.

FIG. 14 is an operational flow of an implementation of a method 1400 for using real time prediction. The method 1400 may be performed by the platform 200 for example. Aspects of the method 1400 may be performed by the prediction engine 250 in some implementations.

At 1410, alternative metabolic inputs, reconciled estimated metabolic inputs, known metabolic inputs, and final estimated metabolic inputs are received, e.g., at the prediction engine 250.

At 1420, at the prediction engine 250, real time prediction is performed using the alternative metabolic inputs, the reconciled estimated metabolic inputs, the known metabolic inputs, and the final estimated metabolic inputs.

At 1430, predicted metabolic states based on the real time prediction are outputted by the replay engine 250.

FIG. 15 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used.

Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 15, an exemplary system for implementing aspects described herein includes a computing device, such as computing device 1500. In its most basic configuration, computing device 1500 typically includes at least one processing unit 1502 and memory 1504. Depending on the exact configuration and type of computing device, memory 1504 may be volatile (such as random access memory (RAM)), non-volatile (such as read-only memory (ROM), flash memory, etc.), or some combination of the two. This most basic configuration is illustrated in FIG. 15 by dashed line 1506.

Computing device 1500 may have additional features/functionality. For example, computing device 1500 may include additional storage (removable and/or non-removable) including, but not limited to, magnetic or optical disks or tape. Such additional storage is illustrated in FIG. 15 by removable storage 1508 and non-removable storage 1510.

Computing device 1500 typically includes a variety of computer readable media. Computer readable media can be any available media that can be accessed by the device 1500 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 1504, removable storage 1508, and non-removable storage 1510 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1500. Any such computer storage media may be part of computing device 1500.

Computing device 1500 may contain communication connection(s) 1512 that allow the device to communicate with other devices. Computing device 1500 may also have input device(s) 1514 such as a keyboard, mouse, pen, voice input device, touch input device, etc. Output device(s) 1516 such as a display, speakers, printer, etc. may also be included. All these devices are well known in the art and need not be discussed at length here.

In an implementation, a method comprises receiving, at an input estimator, untrusted data pertaining to a subject; receiving, at the input estimator, trusted data pertaining to the subject; reconciling, using an input reconciler, the untrusted data using the trusted data; and outputting the reconciled untrusted data.

Implementations may include some or all of the following features. The untrusted data comprises at least one of timing of insulin, amount of insulin, meal data, or activity data. The untrusted data is untrusted because of behavioral anomalies or human error in at least one of timing, amount, estimation, or entry. The trusted data comprises at least one of CGM data, insulin pump data, computer generated data, computer generated models, or an individualized model that describes the glucose and insulin dynamics of the subject. The method further comprises predicting a future glucose state of the subject based on the reconciled untrusted data. The untrusted data comprises reported carbs, wherein the reported carbs are unreliable or unavailable. The untrusted data comprises a stream of data inputs. The method further comprises receiving additional untrusted data and reconciling the additional untrusted data using the trusted data. The method further comprises receiving additional trusted data and reconciling the untrusted data using the additional trusted data. The method further comprises tuning an AP using the reconciled untrusted data. The method further comprises updating a behavior model of the subject using the reconciled untrusted data. The method further comprises determining that the untrusted data is unreliable or unknown. Determining that the untrusted data is unreliable or unknown comprises computing, using modeling, local variance of the untrusted data and comparing the local variance to the overall variance using the untrusted data to determine a comparison amount, wherein when the comparison amount is above a threshold, the untrusted data is determined to be unreliable or unknown. Determining that the untrusted data is unreliable or unknown comprises determining differences between the untrusted data and a model of trusted data.

Implementations may also include some or all of the following features. The method further comprises determining a credibility score for the untrusted data relative to trusted data. The method further comprises generating alerts pertaining to the subject based on the reconciled untrusted data. The method further comprises determining behavior patterns of the subject using the reconciled untrusted data. The method further comprises generating smart alerts pertaining to the subject based on the behavior patterns. The untrusted data comprises diabetes management data. The diabetes management data is estimated diabetes management data. The trusted data comprises diabetes management data corresponding to the estimated diabetes management data, wherein the diabetes management data is received from a connected device or user entry. The method further comprises comparing the untrusted data to the trusted data to identify a behavioral root cause of glycemic dysfunction.

Implementations may also include some or all of the following features. The method further comprises identifying a behavioral root cause of glycemic dysfunction using the reconciled untrusted data. The reconciling comprises: receiving the untrusted data at the input reconciler, wherein the untrusted data comprises untrusted metabolic inputs; receiving the trusted data at the input reconciler, wherein the trusted data comprises estimated untrusted metabolic inputs; and combining the untrusted data and the trusted data using a weighting function to generate reconciled untrusted metabolic inputs. The untrusted data and the trusted data received at the input reconciler are in the form of vectors, and wherein the reconciled untrusted metabolic inputs are in the form of vectors. The weighting function is based on time-relevance. The weighting function is based on relative confidence of the untrusted data and the trusted data. The untrusted data comprises reported untrusted metabolic inputs, and wherein the combining comprises reconciling differences between the reported untrusted metabolic inputs and the estimated untrusted metabolic inputs. The reconciling comprises making the reported untrusted metabolic inputs and the estimated untrusted metabolic inputs consistent with a behavior model. The reconciling comprises reconciling differences between the amount and timing of the untrusted metabolic inputs and the estimated untrusted metabolic inputs with measured data.

In an implementation, a method comprises receiving, at an input estimator, untrusted data pertaining to a subject, wherein the untrusted data comprises user entered data comprising at least one of insulin data, meal data, or activity data; and reconciling, using an input reconciler, the untrusted data using trusted data pertaining to the subject, wherein the trusted data comprises computer generated data.

Implementations may include some or all of the following features. The untrusted data comprises at least one of timing of insulin, amount of insulin, meal data, or activity data. The untrusted data is untrusted because of behavioral anomalies or human error in at least one of timing, amount, estimation, or entry. The trusted data comprises at least one of CGM data, insulin pump data, computer generated models, or an individualized model that describes the glucose and insulin dynamics of the subject. The method further comprises predicting a future glucose state of the subject based on the reconciled untrusted data. The untrusted data comprises reported carbs, wherein the reported carbs are unreliable or unavailable. The untrusted data comprises a stream of data inputs. The method further comprises receiving additional untrusted data and reconciling the additional untrusted data using the trusted data. The method further comprises receiving additional trusted data and reconciling the untrusted data using the additional trusted data. The method further comprises tuning an AP using the reconciled untrusted data. The method further comprises updating a behavior model of the subject using the reconciled untrusted data. The method further comprises determining that the untrusted data is unreliable or unknown. Determining that the untrusted data is unreliable or unknown comprises computing, using modeling, local variance of the untrusted data and comparing the local variance to the overall variance using the untrusted data to determine a comparison amount, wherein when the comparison amount is above a threshold, the untrusted data is determined to be unreliable or unknown. Determining that the untrusted data is unreliable or unknown comprises determining differences between the untrusted data and a model of trusted data. The method further comprises determining a credibility score for the untrusted data relative to trusted data. The method further comprises generating alerts pertaining to the subject based on the reconciled untrusted data. The method further comprises determining behavior patterns of the subject using the reconciled untrusted data. The method further comprises generating smart alerts pertaining to the subject based on the behavior patterns.

Implementations may also include some or all of the following features. The untrusted data comprises diabetes management data. The diabetes management data is estimated diabetes management data. The trusted data comprises diabetes management data corresponding to the estimated diabetes management data, wherein the diabetes management data is received from a connected device or user entry. The method further comprises comparing the untrusted data to the trusted data to identify a behavioral root cause of glycemic dysfunction. The method further comprises identifying a behavioral root cause of glycemic dysfunction using the reconciled untrusted data. The reconciling comprises: receiving the untrusted data at the input reconciler, wherein the untrusted data comprises untrusted metabolic inputs; receiving the trusted data at the input reconciler, wherein the trusted data comprises estimated untrusted metabolic inputs; and combining the untrusted data and the trusted data using a weighting function to generate reconciled untrusted metabolic inputs. The untrusted data and the trusted data received at the input reconciler are in the form of vectors, and wherein the reconciled untrusted metabolic inputs are in the form of vectors. The weighting function is based on time-relevance. The weighting function is based on relative confidence of the untrusted data and the trusted data. The untrusted data comprises reported untrusted metabolic inputs, and wherein the combining comprises reconciling differences between the reported untrusted metabolic inputs and the estimated untrusted metabolic inputs. The reconciling comprises making the reported untrusted metabolic inputs and the estimated untrusted metabolic inputs consistent with a behavior model. The reconciling comprises reconciling differences between the amount and timing of the untrusted metabolic inputs and the estimated untrusted metabolic inputs with measured data. The method further comprises performing replay prediction using the reconciled untrusted data and the trusted data. The method further comprises outputting simulated metabolic states based on the replay prediction. The method further comprises performing real time prediction using the reconciled untrusted data and the trusted data. The method further comprises outputting simulated metabolic states based on the real time prediction.

In an implementation, a method comprises predicting data over a time period for a subject; receiving untrusted data directed to management of diabetes; simulating a plurality of predictive data traces over the time period using a spectrum of possible variances of the untrusted data; comparing the simulated predictive data traces to the predicted data to identify glycemic effects; and outputting a visualization or a recommendation based on the glycemic effects.

Implementations may include some or all of the following features. The untrusted data comprises glucose data, and wherein the predictive data traces comprise predictive glucose traces. Predicting the glucose data is based on trusted CGM data and an individualized model of the glucose-insulin kinetics of the subject. Predicting the glucose data comprises providing a best estimate glucose trace representing glucose state over time. The untrusted data directed to management of diabetes comprises at least one of a timing of insulin, an amount of insulin, meal data, or activity data. The glycemic effects are associated with differences in at least one of an amount of diabetes management data or a timing of diabetes management data.

In an implementation, a system comprises a processor and a metabolic model, wherein the processor is configured to receive untrusted user inputs and reconcile the untrusted user inputs with trusted inputs using the metabolic model.

Implementations may include some or all of the following features. The processor is further configured to optimize the predictive ability of the metabolic model to predict future glucose levels. The processor is further configured to allow a replay of events and outcomes with alternate treatment procedures. The processor is further configured to provide real time prediction of future metabolic states. The processor is further configured to determine the credibility of the untrusted user inputs. The processor is further configured to provide a score corresponding the credibility. The processor is further configured to perform a replay analysis directed to at least one replay application. The at least one replay application comprises assessment of blood glucose (BG) outcome metrics in the analysis, identification of credible instances of scenarios in the replay analysis, evaluation of data quality, credibility profiles, and data credibility as a function of time of day. The processor is further configured to perform a reconciled projection directed to at least one real time application. The at least one real time application comprises confidence of medical actions and determination of need to wait before providing advice.

Implementations may also include some or all of the following features. The untrusted user inputs comprise estimated carbs. The untrusted user inputs comprise a time series of uncertain metabolic inputs. The trusted inputs comprise CGM and insulin pump readings. The trusted inputs comprise a time series of trusted metabolic inputs. The processor is further configured to output estimated metabolic states in time series form, final reconciled estimated metabolic states in time series form, and credibility of final estimated metabolic states and reconciled estimated inputs in time series form. The processor is comprised within a joint state/input estimator, and the metabolic model is a plugin.

In an implementation, a method comprises receiving, at an input estimator, untrusted data pertaining to a subject, wherein the untrusted data comprises user entered data comprising at least one of insulin data, meal data, or activity data; determining, at a credibility assessor, a credibility of the untrusted data; receiving trusted data at the credibility assessor; and updating, at the credibility assessor, the credibility of the untrusted data using the trusted data.

Implementations may include some or all of the following features. Determining the credibility of the untrusted data comprises: determining a first credibility based on at least one of a lack of completeness of the untrusted data or a lack of continuity of the untrusted data; determining a second credibility based on expected behaviors indicative of at least one of the lack of completeness of the untrusted data or the lack of continuity of the untrusted data; determining a third credibility based on artifacts in estimated inputs indicative of systemic unknown factors; and aggregating the first credibility, the second credibility, and the third credibility. Determining the first credibility comprises using measured signals as an input, determining the second credibility comprises using the untrusted data and trusted data as inputs, and determining the third credibility comprises using the untrusted data, estimated untrusted data, and reconciled data as inputs.

In an implementation, a method comprises receiving, at an input estimator, first untrusted data pertaining to a subject, wherein the first untrusted data comprises user entered data comprising at least one of insulin data, meal data, or activity data; determining, at a credibility assessor, a credibility of the first untrusted data; receiving, at the input estimator, second untrusted data pertaining to the subject; determining, at a credibility assessor, a credibility of the second untrusted data; updating, at the credibility assessor, the credibility of the first untrusted data using the second untrusted data or the credibility of the second untrusted data; receiving trusted data at the credibility assessor; and updating, at the credibility assessor, the credibility of the first untrusted data and the second untrusted data using the trusted data.

Implementations may include some or all of the following features. Determining the first credibility of the untrusted data comprises: determining a first credibility based on at least one of a lack of completeness of the untrusted data or a lack of continuity of the untrusted data; determining a second credibility based on expected behaviors indicative of at least one of the lack of completeness of the untrusted data or the lack of continuity of the untrusted data; determining a third credibility based on artifacts in estimated inputs indicative of systemic unknown factors; and aggregating the first credibility, the second credibility, and the third credibility. Determining the first credibility comprises using measured signals as an input, determining the second credibility comprises using the untrusted data and trusted data as inputs, and determining the third credibility comprises using the untrusted data, estimated untrusted data, and reconciled data as inputs.

In an implementation, a method comprises receiving estimated metabolic states, reconciled estimated untrusted metabolic inputs, trusted metabolic inputs, and alternative metabolic inputs; performing replay prediction using the estimated metabolic states, the reconciled estimated untrusted metabolic inputs, the trusted metabolic inputs, and the alternative metabolic inputs; and outputting replay simulated metabolic states based on the replay prediction.

Implementations may include some or all of the following features. The estimated metabolic states, the reconciled estimated untrusted metabolic inputs, and the trusted metabolic inputs each comprise a time series. Performing the replay prediction comprises estimating metabolic states for a duration of the time series for the estimated metabolic states, the reconciled estimated untrusted metabolic inputs, and the trusted metabolic inputs to generate the replay simulated metabolic states.

In an implementation, a method comprises receiving alternative metabolic inputs, reconciled estimated untrusted metabolic inputs, trusted metabolic inputs, and final estimated metabolic inputs; performing real time prediction using the alternative metabolic inputs, the reconciled estimated untrusted metabolic inputs, the trusted metabolic inputs, and the final estimated metabolic inputs; and outputting predicted metabolic states based on the real time prediction.

Implementations may include some or all of the following features. Performing the real time prediction comprises: extrapolating time series for the reconciled estimated untrusted metabolic inputs and the trusted metabolic inputs; and estimating metabolic states into the future using the extrapolated time series, the alternative metabolic inputs, and the final estimated metabolic states. The method further comprises filtering the extrapolated time series to prevent jitter in the predicted metabolic states. The estimated metabolic states are in time series form. The method further comprises filtering the estimated metabolic states to generate the predicted metabolic states. The estimating the metabolic states uses a behavior model of a subject. Extrapolating the time series uses weighting of historical data based on at least one of a time of day, features of a current estimated state, or a database of past metabolic inputs.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method comprising:

receiving, at an input estimator, untrusted data pertaining to a subject, wherein the untrusted data comprises user entered data comprising at least one of untrusted insulin data, untrusted meal data, or untrusted activity data, the untrusted insulin data, the untrusted meal data, and the untrusted activity data each being associated with timing data;

determining, at a credibility assessor, a credibility of the untrusted data;

receiving trusted data at the credibility assessor; and updating, at the credibility assessor, the credibility of the untrusted data using the trusted data;

reconciling differences between the trusted data and the untrusted data to generate reconciled data that includes reconciled insulin data, reconciled meal data, and/or reconciled activity data wherein the reconciled insulin data, reconciled meal data, and/or reconciled activity data are generated at least in part by (i) using a weighted average of the untrusted data and estimated untrusted data, the estimated untrusted data being estimated using the untrusted data, the trusted data and a mathematical model; or (ii) choosing the untrusted data to maximize a classification objective;

performing replay prediction or real time prediction using the trusted data and the reconciled insulin data, the reconciled meal data, and/or the reconciled activity data;

adjusting a therapeutic parameter employed for controlling glucose in a diabetic patient based on the updated credibility of the untrusted data;

optimizing an amount of basal insulin to be delivered to the subject using the adjusted therapeutic parameter; and delivering the optimal amount of basal insulin to the subject using an insulin delivery device.

2. The method of claim 1, wherein determining the credibility of the untrusted data comprises: determining a first credibility based on at least one of a lack of completeness of the untrusted data or a lack of continuity of the untrusted data; determining a second credibility based on expected behaviors indicative of at least one of the lack of completeness of the untrusted data or the lack of continuity of the untrusted data; determining a third credibility based on artifacts in estimated inputs indicative of systemic unknown factors; and aggregating the first credibility, the second credibility, and the third credibility.

3. The method of claim 2, wherein determining the first credibility comprises using measured signals as an input, determining the second credibility comprises using the untrusted data and trusted data as inputs, and determining the third credibility comprises using the untrusted data, estimated untrusted data, and reconciled data as inputs.

4. The method of claim 1 wherein reconciling differences between the trusted data and the untrusted data to generate reconciled data includes estimating values for the untrusted data using an individual mathematical model of metabolic processes to produce or consume glucose.

5. A method comprising:
    receiving, at an input estimator, first untrusted data pertaining to a subject, wherein the first untrusted data comprises user entered data comprising at least one of untrusted insulin data, untrusted meal data, or untrusted activity data, the untrusted insulin data, the untrusted meal data, and the untrusted activity data each being associated with timing data;
    determining, at a credibility assessor, a credibility of the first untrusted data;
    receiving, at the input estimator, second untrusted data pertaining to the subject;
    determining, at a credibility assessor, a credibility of the second untrusted data;
    updating, at the credibility assessor, the credibility of the first untrusted data using the second untrusted data or the credibility of the second untrusted data;
    receiving trusted data at the credibility assessor; and
    updating, at the credibility assessor, the credibility of the first untrusted data and the second untrusted data using the trusted data and reconciling differences between the trusted data and the untrusted data to generate reconciled data that includes reconciled insulin data, reconciled meal data and/or reconciled activity data and reconciled second data, wherein the reconciled insulin data, reconciled meal data, and/or reconciled activity data are generated at least in part by (i) using a weighted average of the untrusted data and estimated untrusted data, the estimated untrusted data being estimated using the untrusted data, the trusted data and a mathematical model; or (ii) choosing the untrusted data to maximize a classification objective;
    performing replay prediction or real time prediction using the trusted data and the reconciled insulin data, the reconciled meal data, and/or the reconciled activity data and the reconciled second data; adjusting a therapeutic parameter employed for controlling glucose in a diabetic patient based on the updated credibility of the first and/or the second untrusted data;
    optimizing an amount of basal insulin to be delivered to the subject using the adjusted therapeutic parameter; and
    delivering the optimal amount of basal insulin to the subject using an insulin delivery device.

6. The method of claim 5, wherein determining the credibility of the first and/or second untrusted data comprises: determining a first credibility based on at least one of a lack of completeness of the first and/or second untrusted data or a lack of continuity of the first and/or second untrusted data; determining a second credibility based on expected behaviors indicative of at least one of the lack of completeness of the first and/or second untrusted data or the lack of continuity of the first and/or second untrusted data; determining a third credibility based on artifacts in estimated inputs indicative of systemic unknown factors; and aggregating the first credibility, the second credibility, and the third credibility.

7. The method of claim 6, wherein determining the first credibility comprises using measured signals as an input, determining the second credibility comprises using the first and/or second untrusted data and trusted data as inputs, and determining the third credibility comprises using the first and/or second untrusted data, estimated untrusted data, and reconciled data as inputs.

8. A system comprising:
    an input estimator configured to receive untrusted data pertaining to a subject, wherein the untrusted data comprises user entered data comprising at least one of untrusted insulin data, untrusted meal data, or untrusted activity data, the untrusted insulin data, the untrusted meal data, and the untrusted activity data each being associated with timing data; and
    a credibility assessor configured to: determine a credibility of the untrusted data, receive trusted data, and update the credibility of the untrusted data using the trusted data;
    an input reconciler configured to reconcile differences between the trusted data and the untrusted data to generate reconciled data that includes reconciled insulin data, reconciled meal data, and/or reconciled activity data, wherein the reconciled insulin data, reconciled meal data, and/or reconciled activity data are generated at least in part by (i) using a weighted average of the untrusted data and estimated untrusted data, the estimated untrusted data being estimated using the untrusted data, the trusted data and a mathematical model; or (ii) choosing the untrusted data to maximize a classification objective;
    a prediction engine configured to perform replay prediction or real time prediction using the trusted data and the reconciled insulin data, the reconciled meal data, and/or the reconciled activity data; a parameter estimator configured to adjust a therapeutic parameter employed for controlling glucose in a diabetic patient based on the updated credibility of the untrusted data; and
    an insulin delivery device delivering an optimal amount of basal insulin to the subject, wherein the optimal amount of basal insulin is optimized using the adjusted therapeutic parameter.

9. The system of claim 8, wherein determining the credibility of the untrusted data comprises: determining a first credibility based on at least one of a lack of completeness of the untrusted data or a lack of continuity of the untrusted data; determining a second credibility based on expected behaviors indicative of at least one of the lack of completeness of the untrusted data or the lack of continuity of the untrusted data; determining a third credibility based on artifacts in estimated inputs indicative of systemic unknown factors; and aggregating the first credibility, the second credibility, and the third credibility.

10. The system of claim 9, wherein determining the first credibility comprises using measured signals as an input, determining the second credibility comprises using the untrusted data and trusted data as inputs, and determining the third credibility comprises using the untrusted data, estimated untrusted data, and reconciled data as inputs.

11. A system comprising:

an input estimator configured to: receive first untrusted data pertaining to a subject, wherein the first untrusted data comprises user entered data comprising at least one of untrusted insulin data, untrusted meal data, or untrusted activity data, and receive second untrusted data pertaining to the subject; and a credibility assessor configured to: determine a credibility of the first untrusted data, determine a credibility of the second untrusted data, update the credibility of the first untrusted data using the second untrusted data or the credibility of the second untrusted data, receive trusted data at the credibility assessor, and update the credibility of the first untrusted data and the second untrusted data using the trusted data;

an input reconciler configured to reconcile differences between the trusted data and the untrusted second data, untrusted insulin data, untrusted meal data and/or untrusted activity data to generate reconciled that includes reconciled second data, reconciled insulin data, reconciled meal data, and/or reconciled activity data, wherein the reconciled insulin data, reconciled meal data, and/or reconciled activity data are generated at least in part by (i) using a weighted average of the untrusted data and estimated untrusted data, the estimated untrusted data being estimated using the untrusted data, the trusted data and a mathematical model; or (ii) choosing the untrusted data to maximize a classification objective;

a prediction engine configured to perform replay prediction or real time prediction using the reconciled data and the trusted data, the reconciled data including the reconciled second data, the reconciled insulin data, the reconciled meal data, and/or the reconciled activity data;

a parameter estimator configured to adjust a therapeutic parameter employed for controlling glucose in a diabetic patient based on the updated credibility of the first and/or second untrusted data; and an insulin delivery device delivering an optimal amount of basal insulin to the subject, wherein the optimal amount of basal insulin is optimized using the adjusted therapeutic parameter.

12. The system of claim 11, wherein determining the credibility of the first and/or second untrusted data comprises: determining a first credibility based on at least one of a lack of completeness of the first and/or second untrusted data or a lack of continuity of the first and/or second untrusted data; determining a second credibility based on expected behaviors indicative of at least one of the lack of completeness of the first and/or second untrusted data or the lack of continuity of the first and/or second untrusted data; determining a third credibility based on artifacts in estimated inputs indicative of systemic unknown factors; and aggregating the first credibility, the second credibility, and the third credibility.

13. The system of claim 12, wherein determining the first credibility comprises using measured signals as an input, determining the second credibility comprises using the first and/or second untrusted data and trusted data as inputs, and determining the third credibility comprises using the untrusted data, estimated untrusted data, and reconciled data as inputs.

* * * * *